(12) United States Patent
Sharonov

(10) Patent No.: US 9,370,392 B2
(45) Date of Patent: Jun. 21, 2016

(54) HEAT-SENSITIVE OPTICAL PROBES

(71) Applicant: COVIDIEN LP, Mansfield, MA (US)

(72) Inventor: Alexey Sharonov, Bethany, CT (US)

(73) Assignee: Covidien LP, Mansfield, MA (US)

( * ) Notice: Subject to any disclaimer, the term of this patent is extended or adjusted under 35 U.S.C. 154(b) by 245 days.

(21) Appl. No.: 13/942,864

(22) Filed: Jul. 16, 2013

(65) Prior Publication Data

US 2014/0094792 A1 Apr. 3, 2014

Related U.S. Application Data

(60) Provisional application No. 61/708,870, filed on Oct. 2, 2012.

(51) Int. Cl.
*A61B 18/12* (2006.01)
*A61B 18/14* (2006.01)
(Continued)

(52) U.S. Cl.
CPC ......... *A61B 18/1233* (2013.01); *A61B 18/1206* (2013.01); *A61B 18/1477* (2013.01);
(Continued)

(58) Field of Classification Search
CPC ...... A61B 18/04; A61B 18/08; A61B 18/082; A61B 18/10; A61B 18/12; A61B 18/1206; A61B 18/1233; A61B 18/14; A61B 18/1477; A61B 18/18; A61B 18/1815; A61B 2018/0016; A61B 2018/00577; A61B 2018/00678; A61B 2018/00702; A61B 2018/00714; A61B 2018/0072; A61B 2018/00755; A61B 2018/00761; A61B 2018/00767; A61B 2018/00791; A61B 2018/00797; A61B 2018/00809; A61B 2018/1425; A61B 2018/1869
USPC ..................................................... 606/33–41
See application file for complete search history.

(56) References Cited

U.S. PATENT DOCUMENTS

D223,367 S 4/1972 Kountz
D263,020 S 2/1982 Rau, III
(Continued)

FOREIGN PATENT DOCUMENTS

CN 1103807 6/1995
DE 390937 3/1924
(Continued)

OTHER PUBLICATIONS

Http://www.posichem.com/english/produkte/farbstoffe/thermochromic.
(Continued)

*Primary Examiner* — Michael Peffley
*Assistant Examiner* — Khadijeh Vahdat

(57) ABSTRACT

A method of directing energy to tissue includes the initial steps of determining target tissue location and/or target tissue margins, positioning an ablation device for delivery of energy to target tissue, and positioning one or more heat-sensitive optical probes into a tissue region to be monitored. Each heat-sensitive optical probe is adapted to utilize spectral properties of light to access one or more optical fiber portions of the heat-sensitive optical probe in response to heat. The method also includes the steps of applying energy to the ablation device, continuing ablation while size and/or position of ablated zone which received heat above a threshold value is displayed on a monitor using one or more electrical signals generated by the one or more heat-sensitive optical probes, determining whether the ablated zone displayed on the monitor is larger than the target tissue margins, and terminating ablation if it is determined that the ablated zone displayed on the monitor is larger than the target tissue margins.

6 Claims, 11 Drawing Sheets

(51) Int. Cl.
*G01K 11/12* (2006.01)
*A61B 18/00* (2006.01)
*A61B 18/18* (2006.01)
*A61B 17/00* (2006.01)

(52) U.S. Cl.
CPC ............ *G01K11/12* (2013.01); *A61B 18/1815* (2013.01); *A61B 2017/0007* (2013.01); *A61B 2018/0016* (2013.01); *A61B 2018/0072* (2013.01); *A61B 2018/00577* (2013.01); *A61B 2018/00678* (2013.01); *A61B 2018/00702* (2013.01); *A61B 2018/00714* (2013.01); *A61B 2018/00755* (2013.01); *A61B 2018/00761* (2013.01); *A61B 2018/00767* (2013.01); *A61B 2018/00791* (2013.01); *A61B 2018/00797* (2013.01); *A61B 2018/00809* (2013.01); *A61B 2018/1425* (2013.01); *A61B 2018/1869* (2013.01)

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| 4,669,475 A | 6/1987 | Turner | |
| D295,893 S | 5/1988 | Sharkany et al. | |
| D295,894 S | 5/1988 | Sharkany et al. | |
| 4,869,259 A | 9/1989 | Elkins | |
| 5,220,927 A | 6/1993 | Astrahan et al. | |
| 5,370,675 A | 12/1994 | Edwards et al. | |
| D354,218 S | 1/1995 | Van de Peer | |
| 5,560,712 A | 10/1996 | Kleinerman | |
| 6,002,968 A | 12/1999 | Edwards | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| 6,478,793 B1 | 11/2002 | Cosman et al. | |
| 6,530,922 B2 | 3/2003 | Cosman et al. | |
| D487,039 S | 2/2004 | Webster et al. | |
| D496,997 S | 10/2004 | Dycus et al. | |
| 6,802,839 B2 | 10/2004 | Behl | |
| D499,181 S | 11/2004 | Dycus et al. | |
| 7,065,394 B2 | 6/2006 | Hobot et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| 7,220,259 B2 | 5/2007 | Harrington et al. | |
| D564,662 S | 3/2008 | Moses et al. | |
| 7,387,626 B2 | 6/2008 | Edwards et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| D681,810 S | 5/2013 | DeCarlo | |
| 2002/0087151 A1 | 7/2002 | Mody et al. | |
| 2003/0083654 A1 | 5/2003 | Chin et al. | |
| 2006/0173359 A1* | 8/2006 | Lin et al. ............ | 600/478 |
| 2006/0224156 A1 | 10/2006 | Arts et al. | |
| 2007/0050000 A1 | 3/2007 | Esch et al. | |
| 2007/0173680 A1 | 7/2007 | Rioux et al. | |
| 2007/0287996 A1 | 12/2007 | Rioux | |
| 2008/0125775 A1 | 5/2008 | Morris | |
| 2008/0183165 A1 | 7/2008 | Buysse et al. | |
| 2010/0249771 A1* | 9/2010 | Pearson et al. ............ | 606/34 |
| 2011/0054459 A1 | 3/2011 | Peterson | |
| 2011/0301590 A1 | 12/2011 | Podhajsky et al. | |
| 2012/0161786 A1 | 6/2012 | Brannan | |
| 2012/0165806 A1 | 6/2012 | Brannan | |

FOREIGN PATENT DOCUMENTS

| | | |
|---|---|---|
| DE | 1099658 | 2/1961 |
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2415263 | 10/1975 |
| DE | 2429021 | 1/1976 |
| DE | 2460481 | 6/1976 |
| DE | 2602517 | 7/1976 |
| DE | 2504280 | 8/1976 |
| DE | 2627679 | 1/1977 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 8712328 | 3/1988 |
| DE | 3711511 | 6/1988 |
| DE | 3904558 | 8/1990 |
| DE | 3942998 | 7/1991 |
| DE | 4238263 | 5/1993 |
| DE | 4303882 | 8/1994 |
| DE | 4339049 | 5/1995 |
| DE | 29616210 | 1/1997 |
| DE | 19608716 | 4/1997 |
| DE | 19751106 | 5/1998 |
| DE | 19717411 | 11/1998 |
| DE | 19751108 | 5/1999 |
| DE | 19801173 | 7/1999 |
| DE | 19848540 | 5/2000 |
| DE | 10224154 | 12/2003 |
| DE | 10310765 | 9/2004 |
| DE | 10328514 | 3/2005 |
| DE | 102004022206 | 12/2005 |
| DE | 202005015147 | 3/2006 |
| DE | 102009015699 | 5/2010 |
| EP | 0 246 350 | 11/1987 |
| EP | 0 521 264 | 1/1993 |
| EP | 0 556 705 | 8/1993 |
| EP | 0 558 429 | 9/1993 |
| EP | 0 836 868 | 4/1998 |
| EP | 0 882 955 | 12/1998 |
| EP | 1 159 926 | 5/2001 |
| EP | 0 648 515 | 4/2003 |
| FR | 179 607 | 11/1906 |
| FR | 1 275 415 | 10/1961 |
| FR | 1 347 865 | 11/1963 |
| FR | 2 235 669 | 1/1975 |
| FR | 2 276 027 | 1/1976 |
| FR | 2 313 708 | 12/1976 |
| FR | 2 502 935 | 10/1982 |
| FR | 2 517 953 | 6/1983 |
| FR | 2 573 301 | 5/1986 |
| FR | 2 862 813 | 5/2005 |
| FR | 2 864 439 | 7/2005 |
| JP | 5-106 | 1/1993 |
| JP | 05-40112 | 2/1993 |
| JP | 06343644 | 12/1994 |
| JP | 07265328 | 10/1995 |
| JP | 08056955 | 3/1996 |
| JP | 08252263 | 10/1996 |
| JP | 09000492 | 1/1997 |
| JP | 09010223 | 1/1997 |
| JP | 11244298 | 9/1999 |
| JP | 2000342599 | 12/2000 |
| JP | 2000350732 | 12/2000 |

(56) References Cited

FOREIGN PATENT DOCUMENTS

| JP | 2001003776 | 1/2001 |
|---|---|---|
| JP | 2001008944 | 1/2001 |
| JP | 2001029356 | 2/2001 |
| JP | 2001037775 | 2/2001 |
| JP | 2001128990 | 5/2001 |
| JP | 2001231870 | 8/2001 |
| JP | 2008142467 | 6/2008 |
| KR | 20070093068 | 9/2007 |
| KR | 20100014406 | 2/2010 |
| KR | 20120055063 | 5/2012 |
| SU | 166452 | 11/1964 |
| SU | 401367 | 11/1974 |
| SU | 727201 | 4/1980 |
| WO | 8702769 A1 | 5/1987 |
| WO | WO00/36985 | 6/2000 |
| WO | WO2010/035831 | 4/2010 |
| WO | 2010102117 A1 | 9/2010 |
| WO | 2012071388 A2 | 5/2012 |

OTHER PUBLICATIONS

Huang, J., J.S. Xu, and R.X. Xu, Heat-sensitive Microbubbles for Intraoperative Assessment of Cancer Ablation Margins. Biomaterials, 2010. 31(6): p. 1278-1286.
European Search Report, Application No. EP 13 18 6382, dated Feb. 27, 2014.
U.S. Appl. No. 13/419,981, filed Mar. 14, 2012, Joseph D. Brannan.
U.S. Appl. No. 13/430,810, filed Mar. 27, 2012, Joseph D. Brannan.
U.S. Appl. No. 13/440,690, filed Apr. 5, 2012, Joseph D. Brannan.
U.S. Appl. No. 13/460,440, filed Apr. 30, 2012, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.
U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
U.S. Appl. No. 13/957,087, filed Aug. 1, 2013, Brannan.
U.S. Appl. No. 13/973,543, filed Aug. 22, 2013, Orszulak.
U.S. Appl. No. 14/011,414, filed Aug. 27, 2013, Ohri.
U.S. Appl. No. 14/011,438, filed Aug. 27, 2013, Ohri.
U.S. Appl. No. 14/014,937, filed Aug. 30, 2013, Willyard.
U.S. Appl. No. 14/017,995, filed Sep. 4, 2013, Brannan.
U.S. Appl. No. 14/018,081, filed Sep. 4, 2013, Brannan.
U.S. Appl. No. 08/136,098, filed Oct. 14, 1993, Roger A. Stern.
U.S. Appl. No. 08/483,742, filed Jun. 7, 1995, Roger A. Stern.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.

Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/Wire Localizer, Namic® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Dumey et al., "Antennas for Medical Applications", Antenna Handbook: Theory Application and Design, p. 24-40, Van Nostrand Reinhold, 1988 New York, V.T. Lo, S.W. Lee.
Carbonell et al., "Comparison of the Gyrus PlasmaKinetic Sealer and the Valleylab LigaSure™ Device in the Hemostasis of Small, Medium, and Large-Sized Arteries" Carolinas Laparoscopic and Advanced Surgery Program, Carolinas Medical Center, Charlotte, NC 2003.
Carus et al., "Initial Experience With The LigaSure™ Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 94 In Biologic Effects of Nonionizing Electromagnetic Fields, CRC Press, Inc., pp. 1424-1428.
Chung et al., "Clinical Experience of Sutureless Closed Hemorrhoidectomy with LigaSure™" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499.
Cosman et al., "Radiofrequency Lesion Generation and its Effect on Tissue Impedence", Applied Neurophysiology, 51:230-242, 1988.
Cosman et al., "Theoretical Aspects of Radiofrequency Lesions in the Dorsal Root Entry Zone" Neurosurgery 15:(1984), pp. 945-950.
Crawford et al., "Use of the LigaSure™ Vessel Sealing System in Urologic Cancer Surger" Grand Rounds In Urology 1999, vol. 1, Issue 4, pp. 10-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" Advanced Input Systems, located at: <http://www.advanced-input.com/lightkey> 2002.

(56) References Cited

OTHER PUBLICATIONS

Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure™ Vessel Sealing System: A Case Report" Innovations That Work, Feb. 2002.
Humphries Jr. et al., "Finite•Element Codes To Model Electrical Heating And Non-LInear Thermal Transport In Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure™ Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure™ Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure™ Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure™ System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.
LigaSure™ Vessel Sealing System, the Seal of Confidence in General, Gynecologic, Urologic, and Laparoascopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSure™ Vessel Sealing System and LigaSure™ Atlas 20 cm Open Instrument" Innovations That Work, Jun. 2003.
Muller et al., "Extended Left Hemicolectomy Using the LigaSure™ Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences•Yingyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSure™ versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure™ Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.

(56) References Cited

OTHER PUBLICATIONS

Sugita et al., "Bipolar Coagulator with Automatic Thermocontrol" J. Neurosurg., vol. 41, Dec. 1944, pp. 777-779.

Sylvain Labonte et al., "Monopole Antennas for Microwave Catheter Ablation", IEEE Trans. on Microwave Theory and Techniques, vol. 44, No. 10, pp. 1832-1840, Oct. 1995.

T. Matsukawa et al., "Percutaneous Microwave Coagulation Therapy in Liver Tumors", Acta Radiologica, vol. 38, pp. 410-415, 1997.

T. Seki et al., (1994) "Ultrasonically Guided Percutaneous Microwave Coagulation Therapy for Small Hepatocellular Carcinoma," Cancer 74(3):817-825.

Urologix, Inc.—Medical Professionals: Targis™ Technology, "Overcoming the Challenge" located at: <http://www.urologix.com-!medicaUtechnology.html > Nov. 18, 1999; 3 pages.

Urrutia et al., (1988). "Retractable-Barb Needle for Breast Lesion Localization: Use in 60 Cases," Radiology 169(3):845-847.

Valleylab Brochure, "Valleylab Electroshield Monitoring System" 2 pages, Nov. 1995.

ValleyLab Brochure, "Electosurgery: A Historical Overview", Innovations in Electrosurgery, 1999.

Vallfors et al., "Automatically Controlled Bipolar Electrocoagulation—'COA-COMP'" Neurosurgical Review 7:2-3 (1984) pp. 187-190.

W. Scott Helton, "LigaSure™ Vessel Sealing System: Revolutionary Hemostasis Product for General Surgery" Sales/Product Literature 1999.

Wald et al., "Accidental Burns", JAMA, Aug. 16, 1971, vol. 217, No. 7, pp. 916-921.

Walt Boyles, "Instrumentation Reference Book", 2002, Butterworth-Heinemann, pp. 262-264.

Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.

\* cited by examiner

HEAT-SENSITIVE OPTICAL PROBES

CROSS REFERENCE TO RELATED APPLICATION

The present application claims the benefit of and priority to U.S. Provisional Application Ser. No. 61/708,870, filed on Oct. 2, 2012, the entire contents of which are incorporated herein by reference.

BACKGROUND

1. Technical Field

The present disclosure relates to systems, devices and methods for performing a medical procedure. More particularly, the present disclosure relates to heat-sensitive optical probes suitable for use during thermal ablation, electrosurgical systems including the same, and methods of directing energy to tissue using the same.

2. Discussion of Related Art

Electrosurgery is the application of electricity and/or electromagnetic energy to cut, dissect, ablate, coagulate, cauterize, seal or otherwise treat biological tissue during a surgical procedure. When electrical energy and/or electromagnetic energy is introduced to tissue, the energy-tissue interaction produces excitation of molecules, creating molecular motion that results in the generation of heat. Electrosurgery is typically performed using a handpiece including a surgical instrument (e.g., end effector, ablation probe, or electrode) adapted to transmit energy to a tissue site during electrosurgical procedures, an electrosurgical generator operable to output energy, and a cable assembly operatively connecting the surgical instrument to the generator.

Treatment of certain diseases requires the destruction of malignant tissue growths, e.g., tumors. Electromagnetic radiation can be used to heat and destroy tumor cells. Treatment may involve inserting ablation probes into tissues where cancerous tumors have been identified. Once the probes are positioned, electromagnetic energy is passed through the probes into surrounding tissue. The application of ultrasound imaging is one of the cost-effective methods often used for tumor localization and ablation device placement.

There are a number of different types of apparatus that can be used to perform ablation procedures. Typically, apparatus for use in ablation procedures include a power generating source, e.g., a microwave or radio frequency (RF) electrosurgical generator, that functions as an energy source, and a surgical instrument (e.g., microwave ablation probe having an antenna assembly) for directing the energy to the target tissue. The generator and surgical instrument are typically operatively coupled by a cable assembly having a plurality of conductors for transmitting energy from the generator to the instrument, and for communicating control, feedback and identification signals between the instrument and the generator.

Using electrosurgical instruments to ablate, seal, cauterize, coagulate, and/or desiccate tissue may result in some degree of thermal injury to surrounding tissue. For example, electrosurgical desiccation may result in undesirable tissue damage due to thermal effects, wherein otherwise healthy tissue surrounding the tissue to which the electrosurgical energy is being applied is thermally damaged by an effect known in the art as "thermal spread". During the occurrence of thermal spread, excess heat from the operative site can be directly conducted to the adjacent tissue and/or the release of steam from the tissue being treated at the operative site can result in damage to the surrounding tissue. The duration of the activation of the generator is directly related to the heat produced in the tissue. The greater the heat produced, the more the potential for thermal spread to adjacent tissues.

Currently available systems and methods for controlling an electrosurgical generator during electrosurgery may include a clinician monitoring and adjusting, as necessary, the amount of energy delivered to a tissue site through current, voltage, impedance, and/or power measurements such that an appropriate tissue effect can be achieved at the tissue site with minimal collateral damage resulting to adjacent tissue. These systems and/or methods typically require a clinician to translate the desired tissue effect to a power setting on an electrosurgical generator and, if necessary, adjust the power setting to compensate for tissue transformations (e.g., desiccation of tissue) associated with the electrosurgical procedure such that a desired tissue effect may be achieved.

It can be difficult to determine the size of an ablated zone and/or to assess the margins of ablated tissue. As can be appreciated, limiting the possibility of thermal spread or the like during an electrosurgical procedure reduces the likelihood of unintentional and/or undesirable collateral damage to surrounding tissue structures which may be adjacent to an intended treatment site. Controlling and/or monitoring the depth of thermal spread during an electrosurgical procedure may aid a clinician in assessing tissue modification and/or transformation during the electrosurgical procedure.

Medical imaging has become a significant component in the clinical setting and in basic physiology and biology research, e.g., due to enhanced spatial resolution, accuracy and contrast mechanisms that have been made widely available. Medical imaging now incorporates a wide variety of modalities that noninvasively capture the structure and function of the human body. Such images are acquired and used in many different ways including medical images for diagnosis, staging and therapeutic management of malignant disease.

Because of their anatomic detail, computed tomography (CT) and magnetic resonance imaging (MRI) are suitable for, among other things, evaluating the proximity of tumors to local structures. CT and MRI scans produce two-dimensional (2-D) axial images, or slices, of the body that may be viewed sequentially by radiologists who visualize or extrapolate from these views actual three-dimensional (3-D) anatomy.

Medical image processing, analysis and visualization play an increasingly significant role in disease diagnosis and monitoring as well as, among other things, surgical planning and monitoring of therapeutic procedures. Unfortunately, tissue heating and thermal damage does not create adequate contrast in ultrasound images to allow determination of the size of an ablated zone and assessment of the margins of ablated tissue.

SUMMARY

A continuing need exists for systems, devices and methods for controlling and/or monitoring real-time tissue effects to improve patient safety, reduce risk, and/or improve patient outcomes. There is a need for intraoperative techniques for ablation margin assessment and feedback control.

According to an aspect of the present disclosure, a method of directing energy to tissue is provided. The method includes the initial steps of determining target tissue location and/or target tissue margins, positioning an ablation device for delivery of energy to target tissue, and positioning one or more heat-sensitive optical probes into a tissue region to be monitored. Each heat-sensitive optical probe is adapted to utilize spectral properties of light to access one or more optical fiber portions of the heat-sensitive optical probe in response to heat. The method also includes the steps of applying energy to the ablation device, continuing ablation while size and/or position of ablated zone which received threshold heat dosage is displayed on a monitor using at least one electrical signal generated by the one or more heat-sensitive optical probes, determining whether the ablated zone displayed on the monitor is larger than the target tissue margins, and if it is determined that the ablated zone displayed on the monitor is larger than the target tissue margins, terminating ablation.

According to another aspect of the present disclosure, an electrosurgical system is provided. The electrosurgical system includes an electrosurgical power generating source, an energy applicator operably associated with the electrosurgical power generating source, a heat-sensitive optical probe adapted to utilize spectral properties of light to access one or more optical fiber portions of the heat-sensitive optical probe in response to heat, and a processor unit communicatively-coupled to the heat-sensitive optical probe. The processor unit is adapted to generate at least one electrical signal for controlling at least one operating parameter associated with the electrosurgical power generating source based at least in part on at least one electrical signal generated by the heat-sensitive optical probe in response to heat.

According to another aspect of the present disclosure, a method of directing energy to tissue is provided. The method includes the initial steps of determining target tissue location and target tissue margins, positioning an energy applicator for delivery of energy to target tissue, and positioning one or more heat-sensitive optical probes into a tissue region to be monitored. Each heat-sensitive optical probe is adapted to utilize spectral properties of light to access one or more optical fiber portions of the heat-sensitive optical probe in response to heat. The method also includes the steps of transmitting energy from an electrosurgical power generating source through the energy applicator to the target tissue; acquiring heat-distribution data representative of a response of at least one optical fiber portion of the at least one heat-sensitive optical probe to the heat generated by the energy transmitted to the target tissue, and determining at least one operating parameter associated with the electrosurgical power generating source based on a tissue ablation rate determined based at least in part on the response of the one or more heat-sensitive optical probes.

In any one of the aspects, the energy applicator may be mechanically-coupled to one or more heat-sensitive optical probes.

In any one of the aspects, the one or more operating parameters associated with the electrosurgical power generating source may be selected from the group consisting of temperature, impedance, power, current, voltage, mode of operation, and duration of application of electromagnetic energy.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second).

As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "transmission line" generally refers to any transmission medium that can be used for the propagation of signals from one point to another.

BRIEF DESCRIPTION OF THE DRAWINGS

Objects and features of the presently-disclosed heat-sensitive optical probe, electrosurgical systems including the same, and methods of directing energy to tissue using the same will become apparent to those of ordinary skill in the art when descriptions of various embodiments thereof are read with reference to the accompanying drawings, of which.

DETAILED DESCRIPTION

Figure 1:
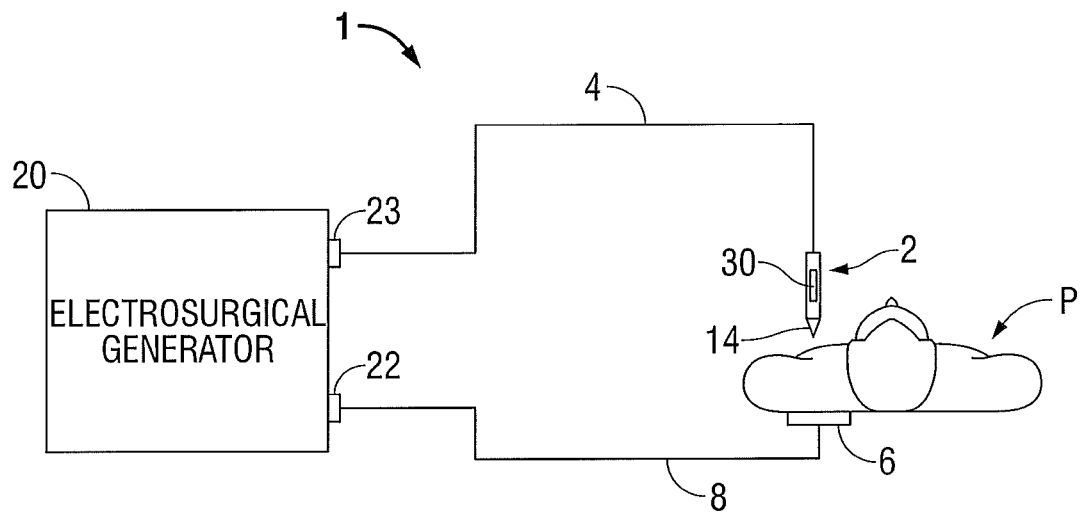
FIG. 1 is a schematic diagram of an electrosurgical system, such as a monopolar electrosurgical system, according to an embodiment of the present disclosure.

Hereinafter, embodiments of the presently-disclosed heat-sensitive optical probe, electrosurgical systems including the same, and methods for directing energy to tissue are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Various embodiments of the present disclosure provide a heat-sensitive optical probe adapted to utilize spectral properties of light to access different portions of the probe. Various embodiments of the present disclosure provide electrosurgical systems and instruments suitable for sealing, cauterizing, coagulating/desiccating and/or cutting vessels and vascular tissue, ablating tissue, or otherwise modifying a tissue or organ of a patient, wherein the presently-disclosed heat-sensitive optical probe is adapted to provide feedback to allow the surgeon to selectively position the energy applicator in tissue during a procedure, and/or may allow the surgeon to adjust, as necessary, of the amount of energy delivered to tissue to facilitate effective execution of a procedure, e.g., an ablation procedure.

Various embodiments of the presently-disclosed electrosurgical systems and instruments use heat-distribution information provided by the presently-disclosed heat-sensitive optical probe to assess the ablation margins and/or the rate of desiccation of tissue. Embodiments may be implemented using electromagnetic energy at RF or microwave frequencies or at other frequencies.

In accordance with embodiments of the present disclosure, one or more operating parameters of an electrosurgical power generating source are adjusted and/or controlled based on the heat-distribution information provided by the presently-disclosed heat-sensitive optical probes, e.g., to maintain a proper ablation rate, or to determine when tissue has been completely desiccated and/or the procedure has been completed.

During a procedure, such as an ablation or other heat treatment procedure, heat may not be uniformly distributed, such as at interfaces having different tissue properties, and accurate monitoring of the ablation may require multi-point measurements of temperature distribution. The above-described heat-sensitive optical probes may be inserted into or placed adjacent to tissue in a variety of configurations, e.g., to allow visual assessment of ablation margins, or to allow the surgeon to determine the rate of ablation and/or when the procedure has been completed, and/or to trigger safety procedures and/or controls, e.g., controls that reduce power level and/or shut off the power delivery to the energy applicator.

Various embodiments of the presently-disclosed electrosurgical systems use heat-distribution information provided by the presently-disclosed heat-sensitive optical probes to trigger safety procedures and/or controls, e.g., controls that reduce power level and/or shuts off the power delivery to the energy applicator, e.g., based on the tissue ablation rate and/or assessment of the ablation margins.

Various embodiments of the presently-disclosed heat-sensitive optical probes are non-sensitive and/or non-reactive to electromagnetic radiation, and monitoring of tissue may be performed in real time while heating, e.g., to allow the surgeon to determine the size of an ablated zone and/or to assess the margins of ablated tissue, and/or to provide real-time feedback to control the ablation or other heat treatment procedure.

The presently-disclosed heat-sensitive optical probes may be used with, mechanically-coupled to, and/or incorporated into any suitable type of handheld medical device or electrosurgical energy delivery device including a handpiece having a surgical instrument, such as, for example, an open device, a catheter-type device, an endoscopic device, and a direct-contact, surface-delivery device.

FIG. 1 schematically illustrates a monopolar electrosurgical system (shown generally as 1) configured to selectively apply electrosurgical energy to target tissue of a patient P. Electrosurgical system 1 generally includes a handpiece 2 coupled via a transmission line 4 to an electrosurgical power generating source 20. Handpiece 2 includes a surgical instrument 14 having one or more electrodes for treating tissue of the patient P (e.g., electrosurgical pencil, electrosurgical cutting probe, ablation electrode(s), etc.). In some embodiments, as shown in FIG. 1, the handpiece 2 includes a control assembly 30. When the electrosurgical energy is applied, the energy travels from the active electrode, to the surgical site, through the patient P and to a return electrode 6 (e.g., a plate positioned on the patient's thigh or back).

Electrosurgical energy is supplied to the instrument 14 by the electrosurgical power generating source 20. Power generating source 20 may be any generator suitable for use with electrosurgical devices to generate energy having a controllable frequency and power level, and may be configured to provide various frequencies of electromagnetic energy. Power generating source 20 may be configured to operate in a variety of modes, such as ablation, monopolar and bipolar cutting, coagulation, and other modes. Control assembly 30 may include a variety of mechanisms adapted to generate signals for adjusting and/or controlling one or more operating parameters (e.g., temperature, impedance, power, current, voltage, mode of operation, and/or duration of application of electromagnetic energy) of the electrosurgical power generating source 20.

The instrument 14 is electrically-coupled via a transmission line, e.g., supply line 4, to an active terminal 23 of the electrosurgical power generating source 20, allowing the instrument 14 to coagulate, ablate and/or otherwise treat tissue. The energy is returned to the electrosurgical power generating source 20 through the return electrode 6 via a transmission line, e.g., return line 8, which is connected to a return terminal 22 of the power generating source 20. In some embodiments, the active terminal 23 and the return terminal 22 may be configured to interface with plugs (not shown) associated with the instrument 14 and the return electrode 6, respectively, e.g., disposed at the ends of the supply line 4 and the return line 8, respectively.

The system 1 may include a plurality of return electrodes 6 that are arranged to minimize the chances of tissue damage by maximizing the overall contact area with the patient P. The power generating source 20 and the return electrode 6 may additionally, or alternatively, be configured for monitoring so-called "tissue-to-patient" contact to ensure that sufficient contact exists therebetween to further minimize chances of tissue damage. The active electrode may be used to operate in a liquid environment, wherein the tissue is submerged in an electrolyte solution.

Figure 2:
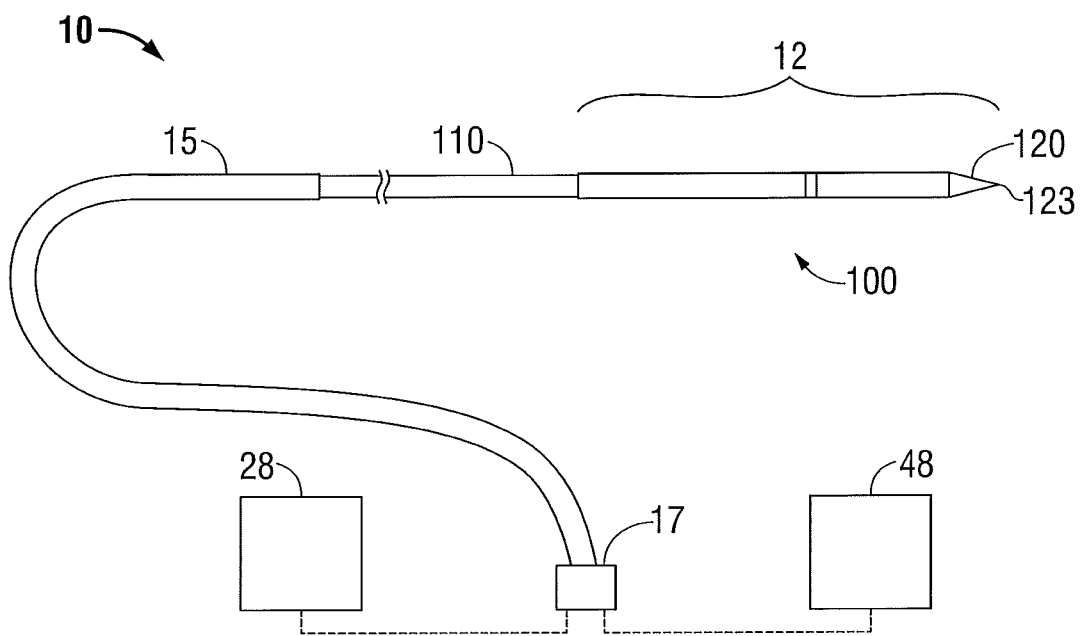
FIG. 2 is a schematic diagram of another embodiment of an electrosurgical system according to the present disclosure.

FIG. 2 schematically illustrates an electrosurgical system (shown generally as 10) including an energy applicator or probe 100. Probe 100 generally includes an antenna assembly 12, and may include a feedline (or shaft) 110 coupled to the antenna assembly 12. Feedline 110 may include a coaxial cable, which may be semi-rigid or flexible. A transmission line 15 may be provided to electrically couple the feedline 110 to an electrosurgical power generating source 28, e.g., a microwave or RF electrosurgical generator.

Feedline 110 may be cooled by fluid, e.g., saline or water, to improve power handling, and may include a stainless steel catheter. Transmission line 15 may additionally, or alternatively, provide a conduit (not shown) configured to provide coolant from a coolant source 48 to the probe 100. In some embodiments, as shown in FIG. 2, the feedline 110 is coupled via a transmission line 15 to a connector 17, which further operably connects the probe 100 to the electrosurgical power generating source 28. Power generating source 28 may be any generator suitable for use with electrosurgical devices, and may be configured to provide various frequencies of energy.

In some embodiments, as shown in FIG. 2, the antenna assembly 12 is a dipole microwave antenna assembly, but other antenna assemblies, e.g., monopole or leaky wave antenna assemblies, may also utilize the principles set forth herein. Located at the distal end of the antenna assembly 12 is an end cap or tapered portion 120, which may terminate in a sharp tip 123 to allow for insertion into tissue with minimal resistance. One example of a straight probe with a sharp tip that may be suitable for use as the energy applicator 100 is commercially available under the trademark EVIDENT™ offered by Covidien Surgical Solutions of Boulder, Colo. The end cap or tapered portion 120 may include other shapes, such as without limitation, a tip 123 that is rounded, flat, square, hexagonal, or cylindroconical.

During microwave ablation, e.g., using the electrosurgical system 10, the probe 100 is inserted into or placed adjacent to tissue and microwave energy is supplied thereto. One or more heat-sensitive optical probes, which are described in more detail later in this description, may be positioned relative to the probe 100 (and/or relative to a target region). Probe 100 may be placed percutaneously or atop tissue, e.g., using conventional surgical techniques by surgical staff. A clinician may pre-determine the length of time that microwave energy is to be applied. The duration of microwave energy application using the probe 100 may depend on the progress of the heat distribution within the tissue area that is to be destroyed and/or the surrounding tissue.

A plurality of probes 100 may be placed in variously arranged configurations to substantially simultaneously ablate a target tissue region, making faster procedures possible. Multiple probes 100 can be used to synergistically create a large ablation or to ablate separate sites simultaneously. Ablation volume is correlated with antenna design, antenna performance, number of energy applicators used simultaneously, ablation time and wattage, and tissue characteristics, e.g., tissue impedance.

In operation, microwave energy having a wavelength, lambda ($\lambda$), is transmitted through the antenna assembly 12 and radiated into the surrounding medium, e.g., tissue. The length of the antenna for efficient radiation may be dependent on the effective wavelength, $\lambda_{eff}$, which is dependent upon the dielectric properties of the treated medium. Antenna assembly 12 through which microwave energy is transmitted at a wavelength, $\lambda$, may have differing effective wavelengths, $\lambda_{eff}$, depending upon the surrounding medium, e.g., liver tissue as opposed to breast tissue.

Figure 3:
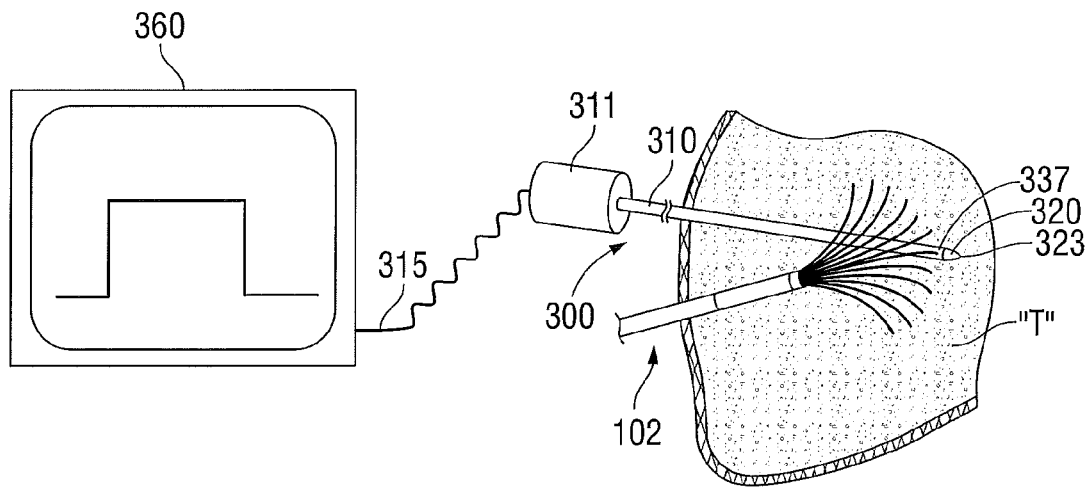
FIG. 3 is a schematic diagram of a heat-sensitive optical probe shown with an RF ablation device positioned for delivery of energy to a tissue region, shown in cross section, according to an embodiment of the present disclosure.
Figure 4:
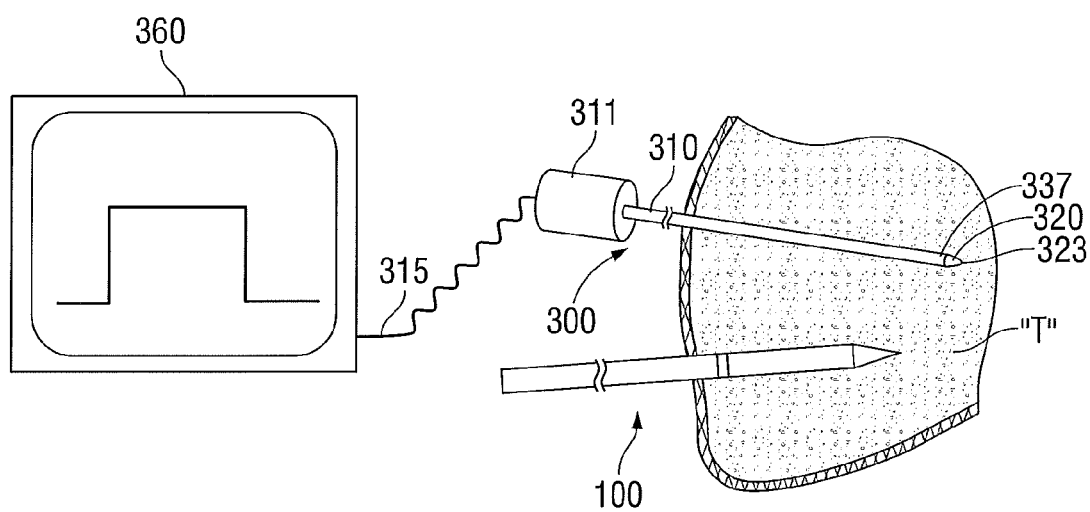
FIG. 4 is a schematic diagram of the heat-sensitive optical probe of FIG. 3 shown with the energy applicator of FIG. 2 positioned for delivery of energy to a tissue region, shown in cross section, according to an embodiment of the present disclosure.

FIGS. 3 and 4 show a heat-sensitive optical probe (shown generally as 300) including an elongated probe member 310 according to an embodiment of the present disclosure. In FIG. 3, the heat-sensitive optical probe 300 is shown positioned in proximity to an RF ablation device 102 positioned for the delivery of energy to target tissue "T". In FIG. 4, the heat-sensitive optical probe 300 is shown positioned in proximity to the energy applicator 100 of FIG. 2 positioned for the delivery of energy to target tissue "T". Heat-sensitive optical probe 300 is adapted to utilize spectral properties of light to access different portions of the probe member 310. An embodiment of a heat-sensitive optical probe suitable for use in tissue ablation applications, such as the heat-sensitive optical probe 300 shown in FIGS. 3 and 4, in accordance with the present disclosure, is shown in more detail in FIG. 5.

A transmission line 315 may be provided to electrically couple the heat-sensitive optical probe 300 to a display device (or screen) 360 such as a flat-panel display, e.g., an LCD (liquid crystal display), plasma display panel (PDP), organic light emitting diode (OLED), or electro-luminescent display (ELD), for providing the user with a variety of output information. In some embodiments, size and/or position of a heated zone which was exposed to a certain degree of heat may be displayed on the display device 360 to provide real-time feedback to the user of the ablation device, e.g., to allow visual assessment of ablation margins, and/or to allow the user to determine the rate of ablation and/or when the procedure has been completed. Heat-sensitive optical probe 300 may include a head portion 311 which may be configured to receive a distal portion of the transmission line 315 therein.

Heat-sensitive optical probe 300 may additionally, or alternatively, include an indicator unit (not shown) adapted to provide a perceptible sensory alert, which may be an audio, visual, or other sensory alarm. The indicator unit may provide a perceptible sensory alert to indicate that a heated zone has received heat above a certain threshold value, or one or more perceptible sensory alerts to allow the user to determine the rate of ablation, or other feedback.

The elongated probe member 310 may be formed of a suitable material, such as a flexible, semi-rigid or rigid material. The heat-sensitive optical probe 300 thickness may be minimized, e.g., to reduce trauma to the surgical site and/or facilitate accurate placement of the device 300 to allow surgeons to treat and/or monitor target tissue with minimal damage to surrounding healthy tissue. In some embodiments, as shown in FIGS. 3 and 4, an end cap or tapered portion 320 is located at the distal end 337 of the probe member 310. The end cap or tapered portion 320 may terminate in a sharp tip 323 to allow for insertion into tissue "T" with minimal resistance. The end cap or tapered portion 320 may include other shapes, such as, for example, a tip 323 that is rounded, flat, square, hexagonal, or cylindroconical.

A variety of medical imaging modalities, e.g., computed tomography (CT) scan or ultrasound, may be used to guide the energy delivery device 102 and/or the heat-sensitive optical probe 300 into the area of tissue "T" to be treated. The shape, size and number of the heat-sensitive optical probe 300 may be varied from the configuration depicted in FIGS. 3 and 4.

Figure 5:
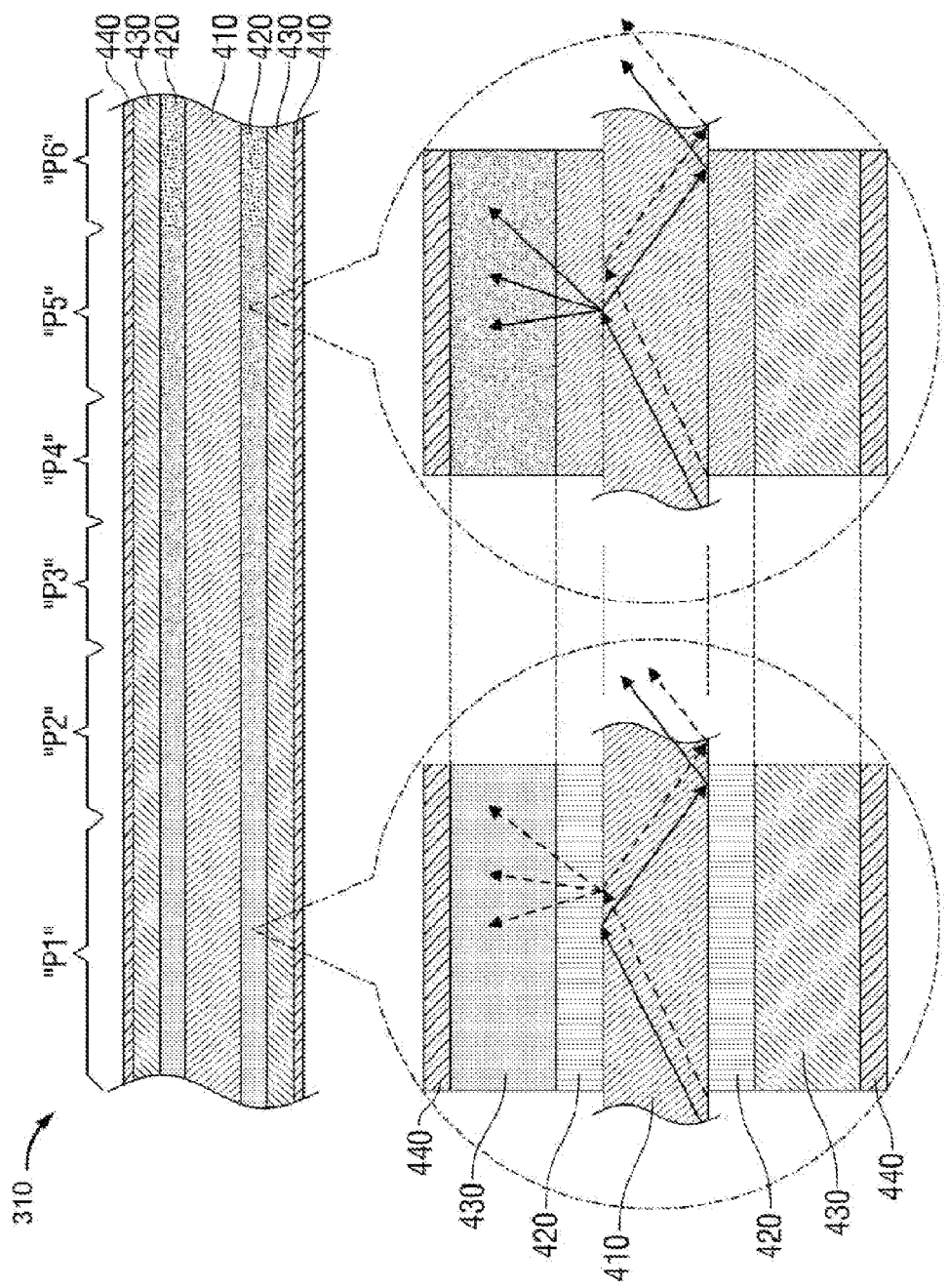
FIG. 5 is an enlarged, cross-sectional view of a portion of the probe member of the heat-sensitive optical probe of FIG. 3 shown with a diagrammatic representation of spectral mapping as a function of heating of the heat-sensitive optical probe according to an embodiment of the present disclosure.

FIG. 5 shows a portion of the probe member 310 of the heat-sensitive optical probe 300 of FIG. 3 shown with a diagrammatic representation of spectral mapping as a function of heating of the heat-sensitive optical probe 300 according to an embodiment of the present disclosure. Heat-sensitive optical probe 300 includes an optical fiber 410 disposed longitudinally within the probe member 310. Optical fiber 410 is optically coupled to a light source (e.g., light source 655 shown in FIG. 6). Optical fiber 410 may longitudinally extend for substantially the entire length of the probe member 320, or portion thereof. In alternative embodiments not shown, the optical fiber 410 may include a plurality of spaced-apart optical fiber segments, which may be independently coupled to one or more light sources.

A color filter 420 characterized by different transparency at different wavelengths is coated, deposited, or otherwise disposed on the optical fiber 410. Color filter 420 may be continuously distributed along the length of heat-sensitive optical probe 300, or the heat-sensitive optical probe 300 may be configured with one or more discrete zones of different color. Heat-sensitive optical probe 300 may include various configurations of a plurality of optical fiber 410 portions individually associated with a plurality of different filter regions (e.g., filter regions of different wavelengths or wavelength bands) to create a color map configuration (e.g., color map 850 shown in FIGS. 8 and 9) to use to assess different portions of the heat-sensitive optical probe 300.

In some embodiments, as shown in FIG. 5, the color filter 420 includes a first filter region of a first characteristic wavelength (e.g., a red light wavelength) disposed in association with a first portion "P1" of the optical fiber 410, a second filter region of a second characteristic wavelength (e.g., a red-orange light wavelength) disposed in association with a second portion "P2", a third filter region of a third characteristic wavelength (e.g., a yellow light wavelength) disposed in association with the third portion "P3", a fourth filter region of a fourth characteristic wavelength (e.g., a yellow-green light wavelength) disposed in association with the fourth portion "P4", a fifth filter region of a fifth characteristic wavelength (e.g., a green light wavelength) disposed in association with the fifth portion "P5", and a sixth filter region of a sixth characteristic wavelength (e.g., a blue light wavelength) disposed in association with the sixth portion "P6" of the optical fiber 410. Although six filter regions of varied characteristic wavelengths of the color filter 420 are shown disposed in association with six portions of the optical fiber 410 in FIG. 5, it is to be understood that any suitable configuration of filter regions of desired characteristic wavelengths may be used.

Light propagating through the color filter 420 may be partially absorbed by the color filter 420; however, light can pass through the color filter 420 in the area that matches the wavelength of the propagating beam. In an illustrative example, as diagrammatically-represented in the lower, left-side enlarged area of detail in FIG. 5, light of a first wavelength (e.g., a red light wavelength, as indicated by the dashed arrowed lines) can pass through the first filter region of the color filter 420 associated with the first portion "P1" of the optical fiber 410, while light of a second wavelength (e.g., a green light wavelength, as indicated by the solid arrowed lines) is absorbed in first portion "P1". Referring to the lower, right-side enlarged area of detail in FIG. 5, light of the second wavelength (e.g., a green light wavelength, as indicated by the solid arrowed lines) can pass through the fifth filter region of the color filter 420 associated with the fifth portion "P5" of the optical fiber 410, while light of the first wavelength (e.g., a red light wavelength, as indicated by the dashed arrowed lines) is absorbed in the fifth portion "P5".

A heat-sensitive material 430 is coated, deposited, or otherwise disposed on the color filter 420. The heat-sensitive material 430 may exhibit change in its optical properties in response to received heat above a certain threshold value. The heat-sensitive material 430 may be absorptive (e.g., thermochromic material, which changes color in response to heat) or diffusive (e.g., scattering material responsive to certain heat level). In some embodiments, the thermochromic material may be a thermochromic dye (or a mixture of thermochromic dyes). The heat-sensitive material 430 response to heat may be reversible, e.g., optical properties return to non-heated configuration when cooled down. The heat-sensitive material 430 response to heat may be non-reversible, e.g., medium remains modified and/or transformed after heat is dissipated.

The heat-sensitive material 430 is covered by an outer shell 440. In some embodiments, the outer shell 640 may be characterized by certain optical properties to optimize response of the heat-sensitive optical probe 300. Outer shell 440 or portions thereof may be transparent, diffusive or reflective. In some embodiments, the outer shell 440 may be constructed of optically transparent material to allow the delivery of radiation from the light source 655 (FIG. 6A), passed through the optical fiber 410, the color filter 420 and the heat-sensitive material 430, to the detector 685. In this configuration, the outer shell 440 acts as an optical guide to deliver the radiation transmitted through the color filter 420 and the heat-sensitive material 430 to the detector 685.

In some embodiments, the internal surface of the outer shell 440 can be made from a diffusive material, e.g., to allow for improved optical coupling. In other embodiments, the inner surface of the outer shell 440 can be made from a reflective material, e.g., to reflect radiation back to the optical fiber 410. The reflected radiation with spectrally encoded response may be delivered to the detector 685 via the same optical fiber 410 as the incoming radiation.

Figure 6A:
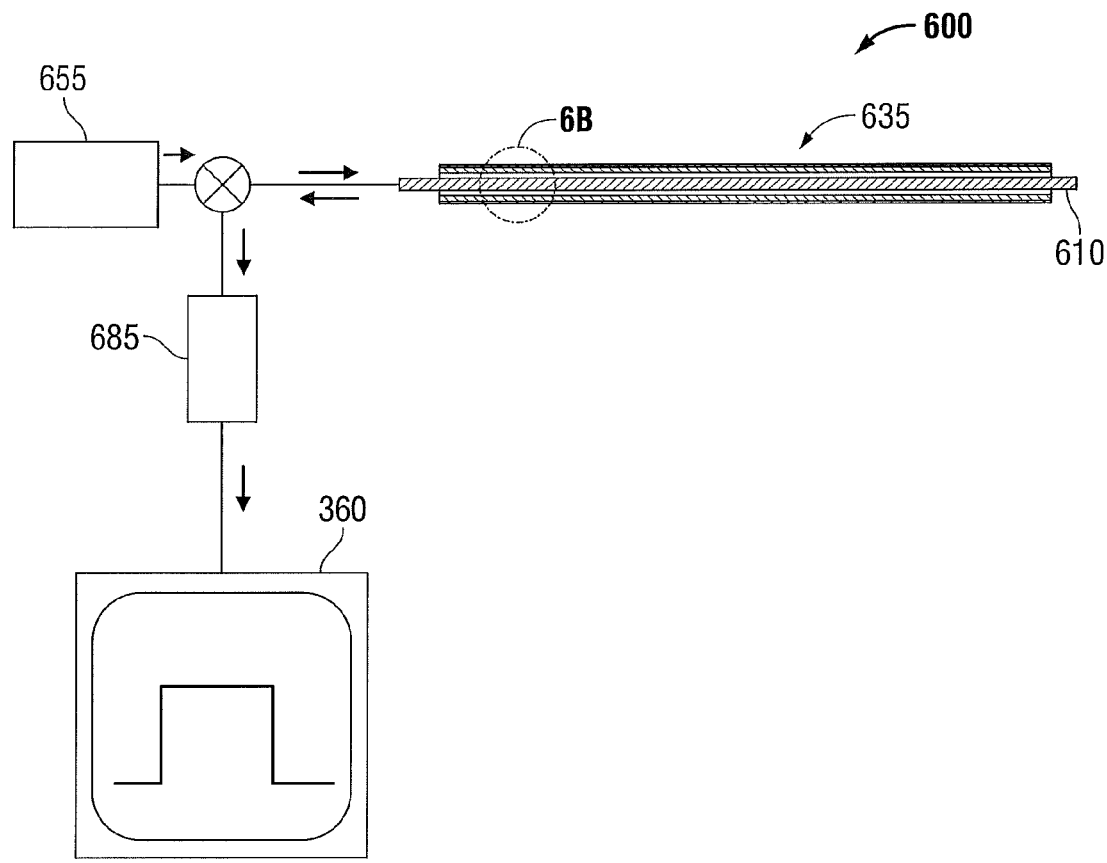
FIG. 6A is a schematic diagram of a system for monitoring heat distribution, such as during an ablation procedure, including a light source and a detector, shown with a portion of a heat-sensitive optical probe, similar to the heat-sensitive optical probe of FIG. 3, shown in cross-section, according to an embodiment of the present disclosure.
Figure 6B:
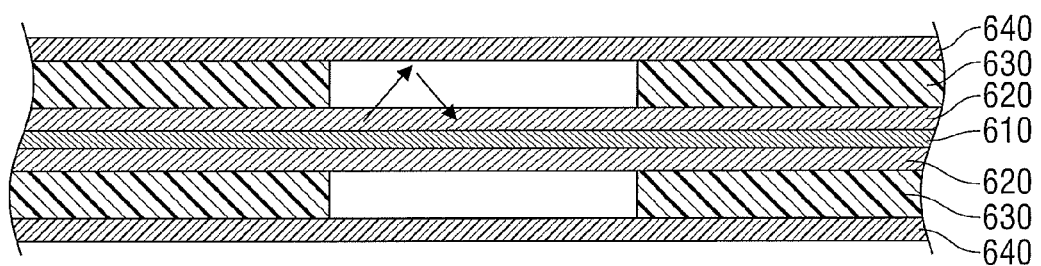
FIG. 6B is an enlarged, longitudinal cross-sectional view of the area of detail indicated in FIG. 6A illustrating a portion of the probe member of the heat-sensitive optical probe, according to an embodiment of the present disclosure.

FIG. 6A shows a system for monitoring heat distribution (shown generally as 600), such as during an ablation procedure, according to an embodiment of the present disclosure that includes a light source 655 and a detector 685, shown with a portion of a heat-sensitive optical probe, similar to the heat-sensitive optical probe 300 of FIG. 3. FIG. 6B shows an enlarged, cross-sectional view of a portion of the probe member 635 of the heat-sensitive optical probe of FIG. 6A.

Referring to FIG. 6B, probe member 635 includes an optical fiber 610 disposed longitudinally within the probe member 635. Optical fiber 610 is optically coupled to a light source 655. A color filter 620 characterized by different transparency at different wavelengths is coated, deposited, or otherwise disposed on the optical fiber 610. Heat-sensitive optical probe 300 may include various configurations of a plurality of optical fiber 610 portions individually associated with a plurality of different filter regions (e.g., filter regions of different wavelengths or wavelength bands) to create a color map configuration (e.g., color map 850 shown in FIGS. 8 and 9) to use to assess different portions of the heat-sensitive optical probe. A heat-sensitive material 630 is coated, deposited, or otherwise disposed on the color filter 620. The heat-sensitive material 630 may exhibit change in its optical properties in response to received heat above a certain threshold value. The heat-sensitive material 630 may be absorptive (e.g., thermochromic material, which changes color in response to heat) or diffusive (e.g., scattering material responsive to certain heat level). In some embodiments, the thermochromic material may be a thermochromic dye (or a mixture of thermochromic dyes). The heat-sensitive material 630 response to heat may be reversible, e.g., optical properties return to non-heated configuration when cooled down. The heat-sensitive material 630 response to heat may be non-reversible, e.g., medium remains modified and/or transformed after heat is dissipated. The heat-sensitive material 630 is covered by an outer shell 640.

Electrosurgical system 600 may include the display device 360 to allow for the presentation of information, such as position and size of one or more regions of the optical probe 600 heated to a certain heat level. For example, if some portion of the probe 600 is heated above a certain level of heat, a spectrally encoded signal from the detector 685 can be decoded by the device 360 to determine position and size of the heated zone. Position (e.g., distance from the proximal or distal end of the probe 600) and zone size may be presented on the display device 360 graphically wherein the heated zone along the optical probe 600 is highlighted either by color or any other method.

The visual assistance provided by the utilization of spectral properties of light to access different portions of the probe member 635 (or probe member 310) of the presently-disclosed heat-sensitive optical probes for providing heat-distribution information on a display device may allow the surgeon to selectively position the energy applicator (e.g., probe 100 shown in FIGS. 2 and 4) in tissue, and/or may allow the surgeon to monitor and adjust, as necessary, the amount of energy delivered to tissue. In some embodiments, one or more electrical signals generated by the heat-sensitive optical probe 300 permits for systems for automated feedback control of one or more parameters associated with an energy delivery device and/or one or more parameters associated with an electrosurgical power generating source (e.g., power generating source 28 shown in FIG. 9), such as to facilitate effective execution of a procedure, e.g., an ablation procedure.

Figure 7A:
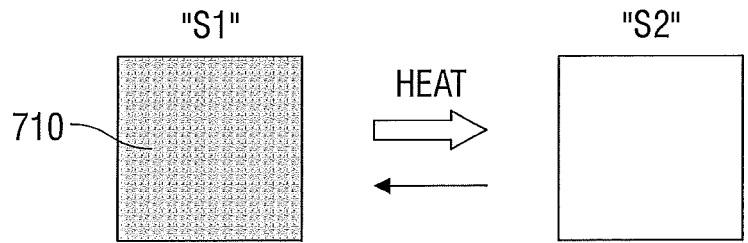
FIG. 7A is a diagrammatic representation of a reversible modification and/or transformation of the optical properties of a media, such as an absorptive medium, according to an embodiment of the present disclosure.

FIG. 7A diagrammatically illustrates a reversible modification and/or transformation of the optical properties of a media 710, from a first state "S1" (e.g., low temperature, color appears) to a second state "S2" (e.g., above transition temperature, colorless), such as in response to the application of heat during thermal ablation. Media 710 may be an absorptive heat-sensitive medium, and may include any of a large number of commercially available dyes and pigments. Media 710 may be any suitable reversible or irreversible thermochromic material capable of changing color in response to temperature stimuli.

In some embodiments, the thermochromic material may be a mixture of thermochromic dyes having different critical temperature limits. As it is used in this description, "critical temperature" of a thermochromic dye generally refers to the temperature at which the color starts changing in response to the temperature stimuli. It may be desirable to adjust dye transition temperature to be in accordance with tissue ablation. Media 710 may be responsive in a wide range of spectrum.

Figure 7B:
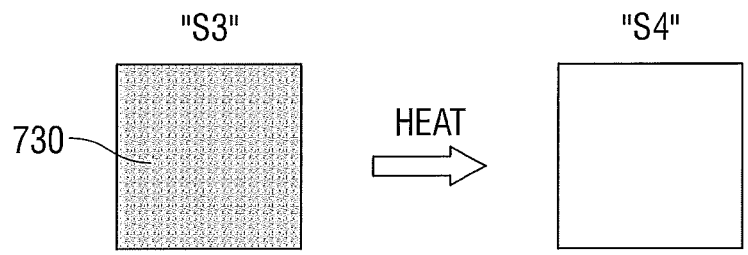
FIG. 7B is a diagrammatic representation of a non-reversible modification and/or transformation of the optical properties of a media, such as an absorptive medium, according to an embodiment of the present disclosure.

FIG. 7B diagrammatically illustrates a non-reversible modification and/or transformation of the optical properties of a media 730, e.g., an absorptive medium, from a first state "S3" (e.g., low temperature, color appears) to a second state "S4" (e.g., above transition temperature, colorless), such as in response to the application of heat during thermal ablation. Media 710 may be an absorptive heat-sensitive medium, and may be responsive in a wide range of spectrum.

Figure 7C:
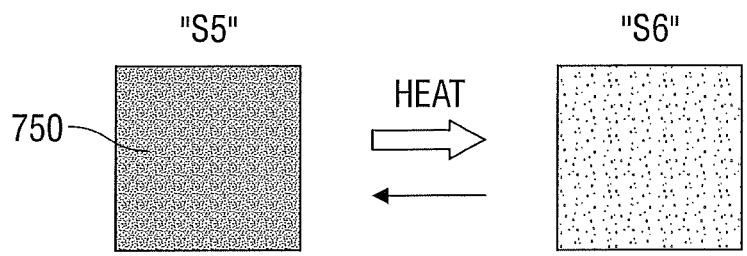
FIG. 7C is a diagrammatic representation of a reversible modification and/or transformation of the optical properties of a media, such as a diffusive medium, according to an embodiment of the present disclosure.

FIG. 7C diagrammatically illustrates a reversible modification and/or transformation of the optical properties of a media 750, from a first state "S5" (e.g., low temperature, low scattering) to a second state "S6" (e.g., high temperature, high scattering), such as in response to the application of heat during thermal ablation. Media 750 may be a diffusive heat-sensitive medium, and may be responsive in a wide range of spectrum. A layer of diffusive heat-sensitive material after transition to liquid phase may drastically change scattering properties.

Figure 7D:
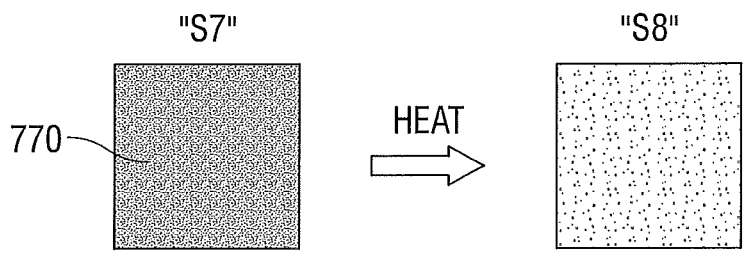
FIG. 7D is a diagrammatic representation of a non-reversible modification and/or transformation of the optical properties of a media, such as a diffusive medium, according to an embodiment of the present disclosure.

FIG. 7D diagrammatically illustrates a non-reversible modification and/or transformation of the optical properties of a media 770, from a first state "S7" (e.g., low temperature, low scattering) to a second state "S8" (e.g., high temperature, high scattering), such as in response to the application of heat during thermal ablation. Media 770 may be responsive in a wide range of spectrum. In some embodiments, the media 770 may be a diffusive heat-sensitive medium, and may be composed of a substance (e.g., polymer) with appropriate melting temperature.

Figure 8:
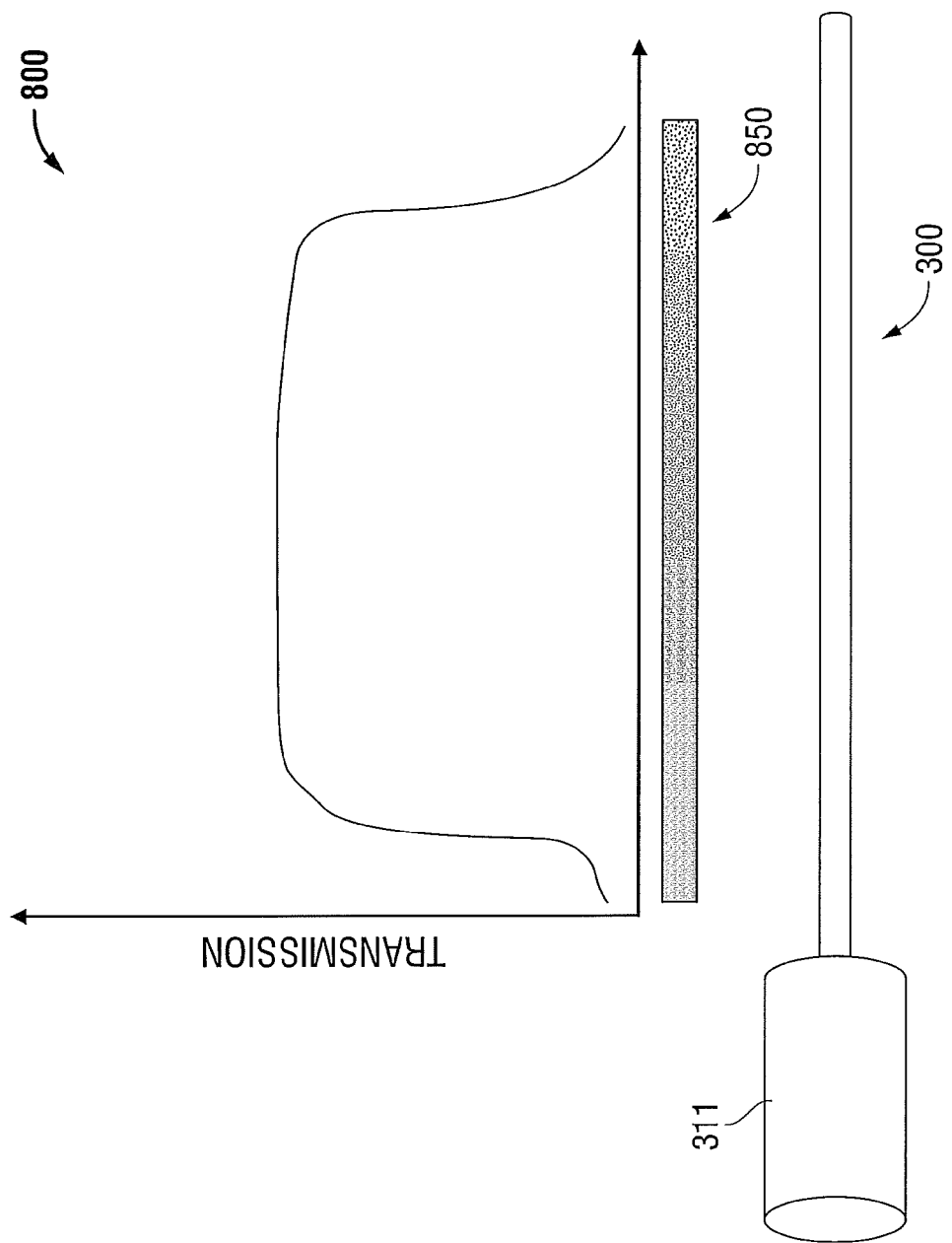
FIG. 8 is a schematic diagram of the heat-sensitive optical probe of FIG. 3, shown with a graph depicting a configuration of a color map diagrammatically represented and plotted against transmission, prior to ablation, according to an embodiment of the present disclosure.

FIG. 8 is a schematic diagram of the heat-sensitive optical probe 300 of FIG. 3 shown with a graph depicting a diagrammatically-represented color map 850 associated with the heat-sensitive optical probe 300 plotted against transmission, prior to thermal ablation, according to an embodiment of the present disclosure. In some embodiments, wherein a broadband light source (white light) is used to deliver light to the heat-sensitive optical probe 300. Before heating, the original response after calibration and adjustments for wavelength sensitivity is flat, as shown in FIG. 8

Figure 9:
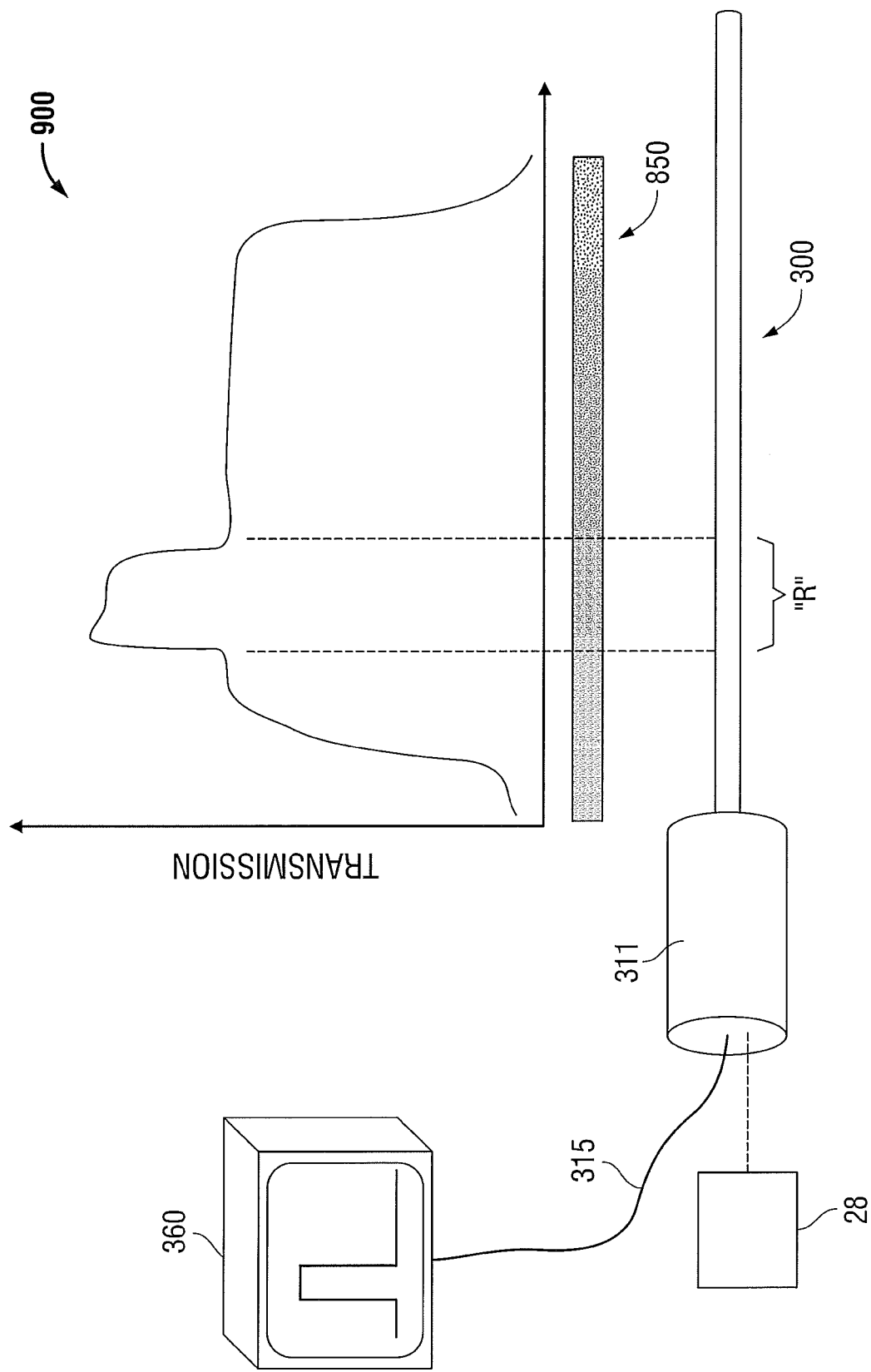
FIG. 9 is a schematic diagram of the heat-sensitive optical probe of FIG. 3, shown with a graph depicting a configuration of a color map diagrammatically represented and plotted against transmission, during ablation, according to an embodiment of the present disclosure.

If some region of the probe 300 (depicted as "R" in FIG. 9) is heated and receives a certain level of heat, changes in optical transmission of the thermosensitive layer in this region causes changes in optical response, thus the spectrally encoded response of the probe because of heat. The spectrally encoded signal(s) contains information relating to the location of the heated region (spectral mapping). For example, as shown in FIG. 9, the originally flat response from broadband light source (FIG. 8) is no longer flat if some portion of thermo sensitive layer changes its transparency because of heating. The probe 300 is constructed such that when every portion of the probe 300 associated with unique color of the color filter, a spectrally-encoded response can be decoded by device 360, e.g., to determine which region of the probe 300 was heated.

Figure 10:
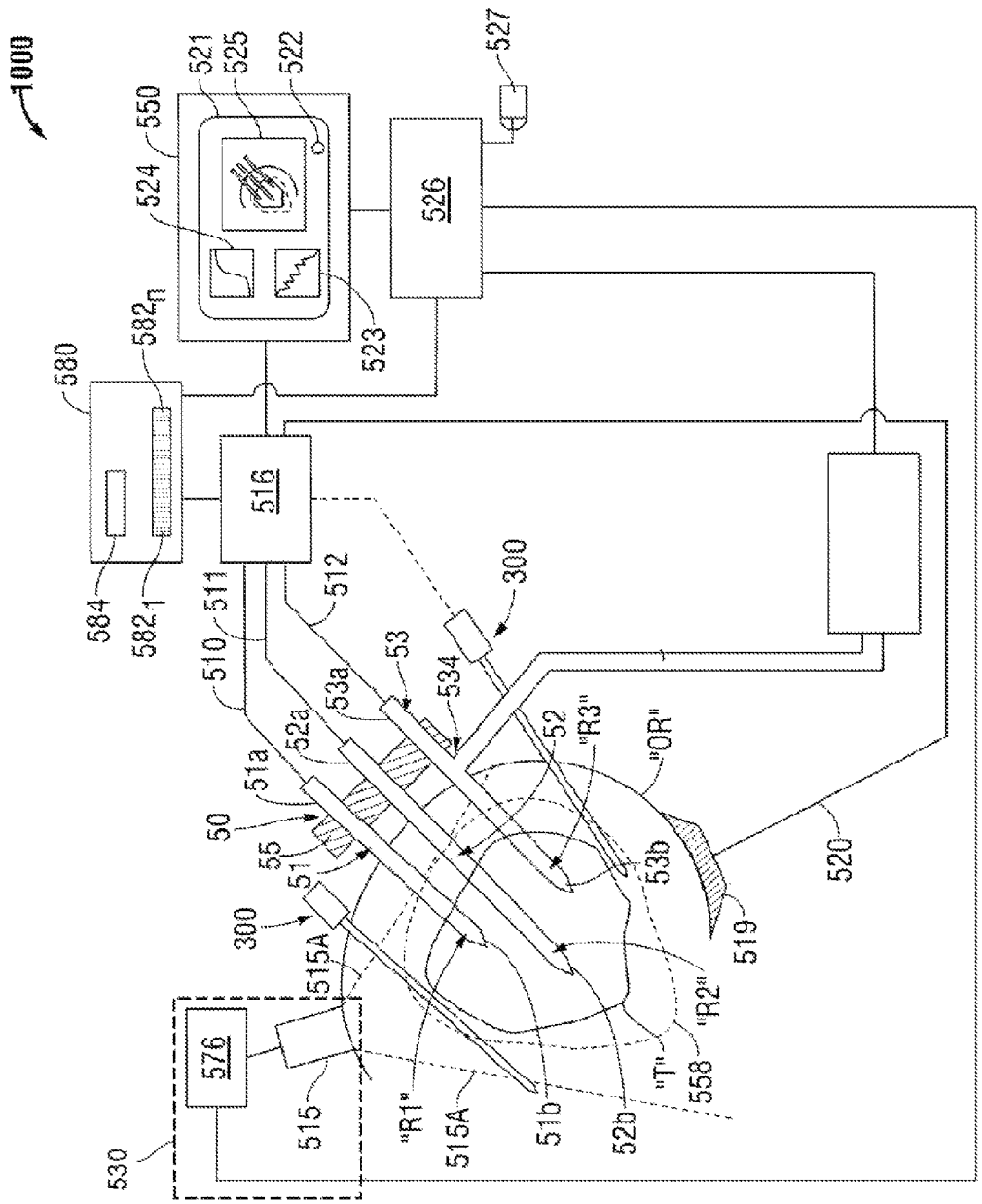
FIG. 10 is a schematic diagram of an electrosurgical system including the heat-sensitive optical probe of FIG. 3 shown with an energy applicator array positioned for the delivery of energy to target tissue according to an embodiment of the present disclosure.

FIG. 10 schematically illustrates an electrosurgical system (shown generally as 1000) according to an embodiment of the present disclosure that includes an electromagnetic energy delivery device or energy applicator array 50 positioned for the delivery of energy to a target region "T". Energy applicator array 50 may include one or more energy applicators or probes.

In some embodiments, as shown in FIG. 10, the electrosurgical system 1000 includes two heat-sensitive optical probes 300. It is to be understood that any suitable number of heat-sensitive optical probes 300 may be used. In some embodiments, one or more heat-sensitive optical probes may additionally, or alternatively, be mechanically-coupled to the energy delivery device or component thereof (e.g., support member 56 of the energy delivery device 60 shown in FIG. 11). The relative positioning of the heat-sensitive optical probe 300 may be varied from the configuration depicted in FIG. 10.

In the embodiment shown in FIG. 10, the energy applicator array 50 includes three probes 51, 52 and 53 having different lengths and arranged substantially parallel to each other. The probes may have similar or different diameters, may extend to equal or different lengths, and may have a distal end with a tapered tip. In some embodiments, the probe(s) may be provided with a coolant chamber, and may be integrally associated with a hub (e.g., hub 534 shown in FIG. 10) that provides electrical and/or coolant connections to the probe(s). Additionally, or alternatively, the probe(s) may include coolant inflow and outflow ports to facilitate the flow of coolant into, and out of, the coolant chamber.

Probes 51, 52 and 53 generally include a radiating section "R1", "R2" and "R3", respectively, operably connected by a feedline (or shaft) 51a, 52a and 53a, respectively, to an electrosurgical power generating source 516, e.g., a microwave or RF electrosurgical generator. In some embodiments, the power generating source 516 is configured to provide microwave energy at an operational frequency from about 300 MHz to about 10 GHz. Power generating source 516 may be configured to provide various frequencies of electromagnetic energy.

Transmission lines 510, 511 and 512 may be provided to electrically couple the feedlines 51a, 52a and 53a, respectively, to the electrosurgical power generating source 516. Located at the distal end of each probe 51, 52 and 53 is a tip portion 51b, 52b and 53b, respectively, which may be configured to be inserted into an organ "OR" of a human body or any other body tissue. Tip portion 51b, 52b and 53b may terminate in a sharp tip to allow for insertion into tissue with minimal resistance. The shape, size and number of probes of the energy applicator array 50 may be varied from the configuration depicted in FIG. 10.

Electrosurgical system 1000 according to embodiments of the present disclosure includes a user interface 550. User interface 550 may include a display device 521, such as without limitation a flat panel graphic LCD (liquid crystal display), adapted to visually display one or more user interface elements (e.g., 523, 524 and 525 shown in FIG. 10). In an embodiment, the display device 521 includes touchscreen capability, e.g., the ability to receive user input through direct physical interaction with the display device 521, e.g., by contacting the display panel of the display device 521 with a stylus or fingertip.

User interface 550 may additionally, or alternatively, include one or more controls 522 that may include without limitation a switch (e.g., pushbutton switch, toggle switch, slide switch) and/or a continuous actuator (e.g., rotary or linear potentiometer, rotary or linear encoder). In an embodiment, a control 522 has a dedicated function, e.g., display contrast, power on/off, and the like. Control 522 may also have a function that may vary in accordance with an operational mode of the electrosurgical system 1000. A user interface element (e.g., 523 shown in FIG. 10) may be provided to indicate the function of the control 522.

As shown in FIG. 10, the electrosurgical system 1000 may include a reference electrode 519 (also referred to herein as a "return" electrode). Return electrode 519 may be electrically coupled via a transmission line 520 to the power generating source 516. During a procedure, the return electrode 519 may be positioned in contact with the skin of the patient or a surface of the organ "OR". When the surgeon activates the energy applicator array 50, the return electrode 519 and the transmission line 520 may serve as a return current path for the current flowing from the power generating source 516 through the probes 51, 52 and 53.

During microwave ablation, e.g., using the electrosurgical system 1000, the energy applicator array "E" is inserted into or placed adjacent to tissue and microwave energy is supplied thereto. Ultrasound or computed tomography (CT) guidance may be used to accurately guide the energy applicator array 50 into the area of tissue to be treated. A clinician may pre-determine the length of time that microwave energy is to be applied. Application duration may depend on a variety of factors such as energy applicator design, number of energy applicators used simultaneously, tumor size and location, and whether the tumor was a secondary or primary cancer. The duration of microwave energy application using the energy applicator array 50 may depend on the progress of the heat distribution within the tissue area that is to be destroyed and/or the surrounding tissue.

FIG. 10 shows a target region including ablation target tissue represented in sectional view by the solid line "T". It may be desirable to ablate the target region "T" by fully engulfing the target region "T" in a volume of lethal heat elevation. Target region "T" may be, for example, a tumor that has been detected by a medical imaging system 530.

Medical imaging system 530, according to various embodiments, includes one or more image acquisition devices (e.g., scanner 515 shown in FIG. 10) of any suitable imaging modality. Medical imaging system 530 may additionally, or alternatively, include a medical imager (not shown) operable to form a visible representation of the image based on the input pixel data. Medical imaging system 530 may include a computer-readable storage medium such as an internal memory unit 576, which may include an internal memory card and removable memory, capable of storing image data representative of an ultrasound image (and/or images from other modalities) received from the scanner 515. In some embodiments, the medical imaging system 530 may be a multi-modal imaging system capable of scanning using different modalities. Medical imaging system 530, according to embodiments of the present disclosure, may include any device capable of generating digital data representing an anatomical region of interest.

Image data representative of one or more images may be communicated between the medical imaging system 530 and a processor unit 526. Medical imaging system 530 and the processor unit 526 may utilize wired communication and/or wireless communication. Processor unit 526 may include any type of computing device, computational circuit, or any type of processor or processing circuit capable of executing a series of instructions that are stored in a computer-readable storage medium (not shown), which may be any device or medium that can store code and/or data. Processor unit 526 may be adapted to run an operating system platform and application programs. Processor unit 526 may receive user inputs from a keyboard (not shown), a pointing device 527, e.g., a mouse, joystick or trackball, and/or other device communicatively-coupled to the processor unit 526.

As shown in FIG. 10, a scanner 515 of any suitable imaging modality may be disposed in contact with the organ "OR" to provide image data. As an illustrative example, the two dashed lines 515A in FIG. 10 bound a region for examination by the scanner 515, e.g., a real-time ultrasonic scanner.

In FIG. 10, the dashed line 558 surrounding the target region "T" represents the ablation isotherm in a sectional view through the organ "OR". Such an ablation isotherm may be that of the surface achieving possible temperatures of approximately 50° C. or greater. The shape and size of the ablation isotherm volume, as illustrated by the dashed line 558, may be influenced by a variety of factors including the configuration of the energy applicator array 50, the geometry of the radiating sections "R1", "R2" and "R3", cooling of the probes 51, 52 and 53, ablation time and wattage, and tissue characteristics.

Processor unit 526 may be connected to one or more display devices (e.g., 521 shown in FIG. 10) for displaying output from the processor unit 26, which may be used by the clinician to visualize the target region "T", the ablation isotherm volume 558, and/or the ablation margins in real-time, or near real-time, during a procedure, e.g., an ablation procedure.

In some embodiments, real-time data and/or near real-time data acquired from heat-sensitive optical probes 300 that includes heat-distribution information, e.g., data representative of one or more filter regions of the heat-sensitive optical probe 300 during an ablation procedure, may be outputted from the processor unit 526 to one or more display devices. Processor unit 526 is adapted to analyze image data including heat-distribution information to determine one or more parameters associated with the energy applicator array 50 and/or one or more parameters associated with the electrosurgical power generating source 516 e.g., based on the tissue ablation rate and/or assessment of the ablation margins.

Electrosurgical system 1000 may include a library 580 including a plurality of heat-sensitive optical probe 300 (and/or optical fiber 610 portion) profiles or overlays $582_1$-$582_n$. As it is used in this description, "library" generally refers to any repository, databank, database, cache, storage unit and the like. Each of the overlays $582_1$-$582_n$ may include a thermal profile that is characteristic of and/or specific to particular heat-sensitive optical probe configurations, e.g., color map configuration, and/or exposure time.

Library 580 according to embodiments of the present disclosure may include a database 584 that is configured to store and retrieve energy applicator data, e.g., parameters associated with one or more energy applicators (e.g., 51, 52 and 53 shown in FIG. 10) and/or one or more energy applicator arrays (e.g., 50 shown in FIG. 10) and/or parameters associated with one or more heat-sensitive optical probes 300 and/or portions of the optical fiber 610 thereof (e.g., optical fiber portions "P1", "P2", "P3", "P4", "P5" and "P6" shown in FIG. 5). Images and/or non-graphical data stored in the library 580, and/or retrievable from a PACS database (not shown), may be used to configure the electrosurgical system 1000 and/or control operations thereof. For example, heat-distribution information, e.g., data representative of one or more heat-sensitive optical probes 300 and/or portions of the optical fiber 610 thereof and/or filter regions associated therewith during an ablation procedure, according to embodiments of the present disclosure, may be used as a feedback tool to control an instrument's and/or clinician's motion, e.g., to allow clinicians to avoid ablating certain structures, such as large vessels, healthy organs or vital membrane barriers.

Figure 11:
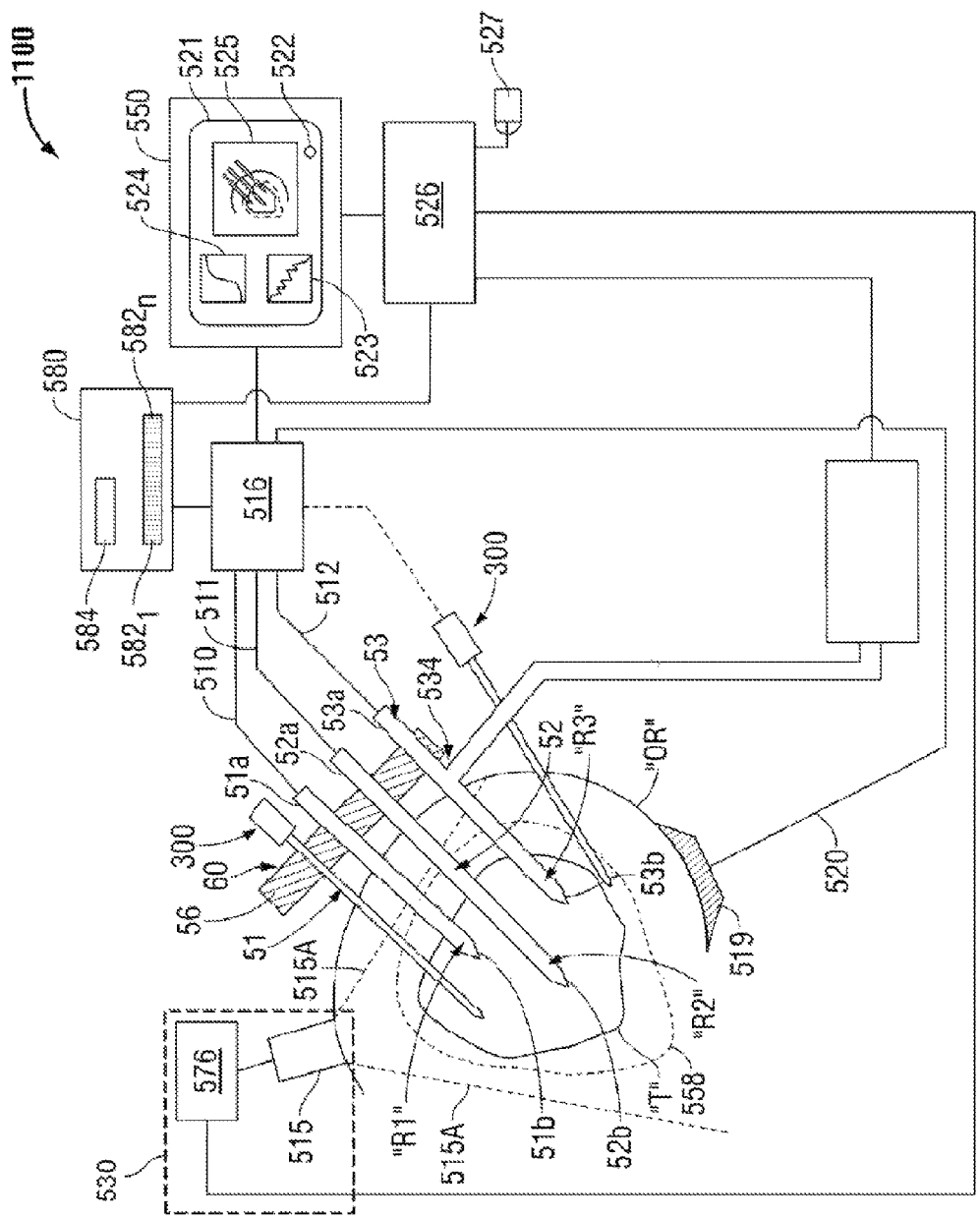
FIG. 11 is a schematic diagram of an electrosurgical system similar to the electrosurgical system of FIG. 10, except for the configuration of the energy delivery device, according to an embodiment of the present disclosure.

FIG. 11 schematically illustrates an electrosurgical system (shown generally as 1100) according to an embodiment of the present disclosure that is similar to the electrosurgical system 1000 of FIG. 10, except for the configuration of the electromagnetic energy delivery device (or energy applicator array) 60, and further description of the same components as those of the electrosurgical system of FIG. 10 is omitted in the interests of brevity.

Energy applicator array 60 includes the probes 51, 52 and 53 of FIG. 10 and a support member 56 configured to provide support to the probes 51, 52 and 53. Support member 56 is similar to the support member 55 of the energy applicator array 50 shown in FIG. 10, except that the support member 56 of FIG. 11 is configured to support a heat-sensitive optical probe 300. In some embodiments, the heat-sensitive optical probe 300 may be removeably coupleable to the support member 56. In alternative embodiments not shown, the support member 56 may be configured to support a plurality of heat-sensitive optical probes 300, which may be positioned at any of a variety of locations relative to the probes 51, 52 and 53.

In FIG. 7, the heat-sensitive optical probe 300 of FIG. 3A is shown positioned in proximity to an energy delivery device 750 positioned for delivery of energy to a region of tissue "T". A variety of medical imaging modalities, e.g., computed tomography (CT) scan or ultrasound, may be used to guide the energy delivery device 750 and/or the heat-sensitive optical probe 300 into the area of tissue "T" to be treated.

Hereinafter, methods of directing energy to tissue are described with reference to FIGS. 12 and 13. It is to be understood that the steps of the methods provided herein may be performed in combination and in a different order than presented herein without departing from the scope of the disclosure.

Figure 12:
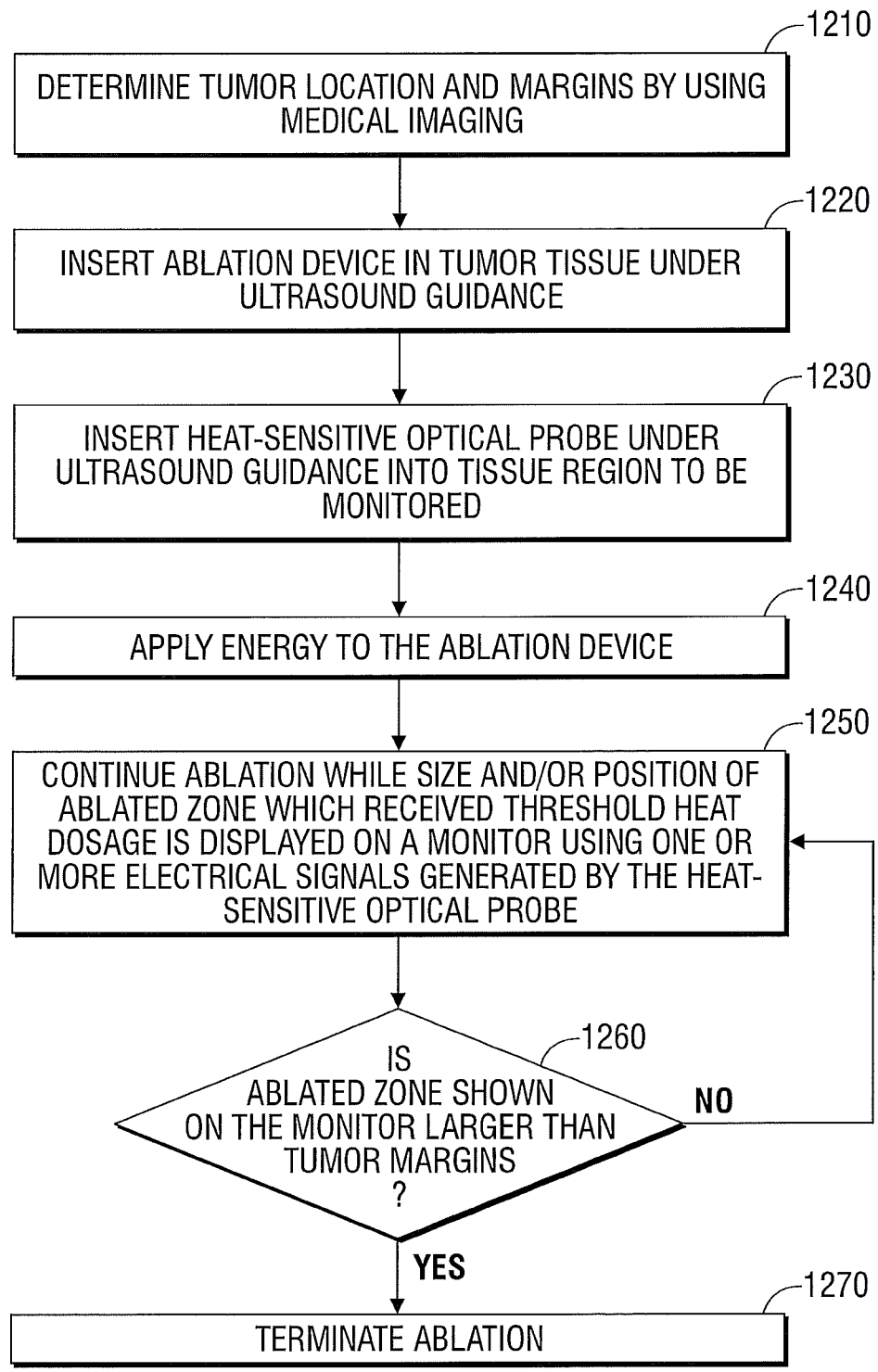
FIG. 12 is a flowchart illustrating a method of directing energy to tissue in accordance with an embodiment of the present disclosure.

FIG. 12 is a flowchart illustrating a method of directing energy to tissue according to an embodiment of the present disclosure. In step 1210, target tissue (e.g., tumor) "T" location and/or target tissue "T" margins are determined by using medical imaging. Any suitable medical imaging techniques may be used, e.g., ultrasound, magnetic resonance imaging (MRI), or computed tomography (CT) imaging.

In step 1220, an ablation device (e.g., energy applicator 60) is positioned for delivery of energy to target tissue "T". The energy applicator may be inserted directly into tissue "T", inserted through a lumen, e.g., a vein, needle or catheter, placed into the body during surgery by a clinician, or positioned in the body by other suitable methods. Ultrasound guidance may be used to guide the energy applicator 60 into the area of tissue "T" to be treated. The energy applicator 60 is operably associated with an electrosurgical power generating source 516.

In step 1230, a heat-sensitive optical probe 300 is positioned into the tissue region to be monitored. Ultrasound guidance may be used to guide the heat-sensitive optical probe 300 into the area of tissue "T" to be monitored. Heat-sensitive optical probe 300 is adapted to utilize spectral properties of light to access one or more optical fiber portions (e.g., optical fiber portions "P1", "P2", "P3", "P4", "P5" and "P6") of the heat-sensitive optical probe 300 in response to heat.

In step 1240, energy from the electrosurgical power generating source 516 is applied to the energy applicator 60. The electrosurgical power generating source 516 may be capable of generating energy at RF or microwave frequencies or at other frequencies.

In step 1250, ablation continues while the size and/or position of an ablated zone which received heat above a certain threshold value is displayed on a monitor using one or more electrical signals generated by the one or more heat-sensitive optical probes 300.

In step 1260, a determination is made whether the ablated zone shown on the monitor is larger than the tumor margins determined in step 1210.

If it is determined, in step 1260, that the ablated zone shown on the monitor is larger than the tumor margins, then, ablation is terminated, in step 1270. Otherwise, if it is determined, in step 1260, that the ablated zone shown on the monitor is not larger than the tumor margins, then repeat step 1250.

Figure 13:
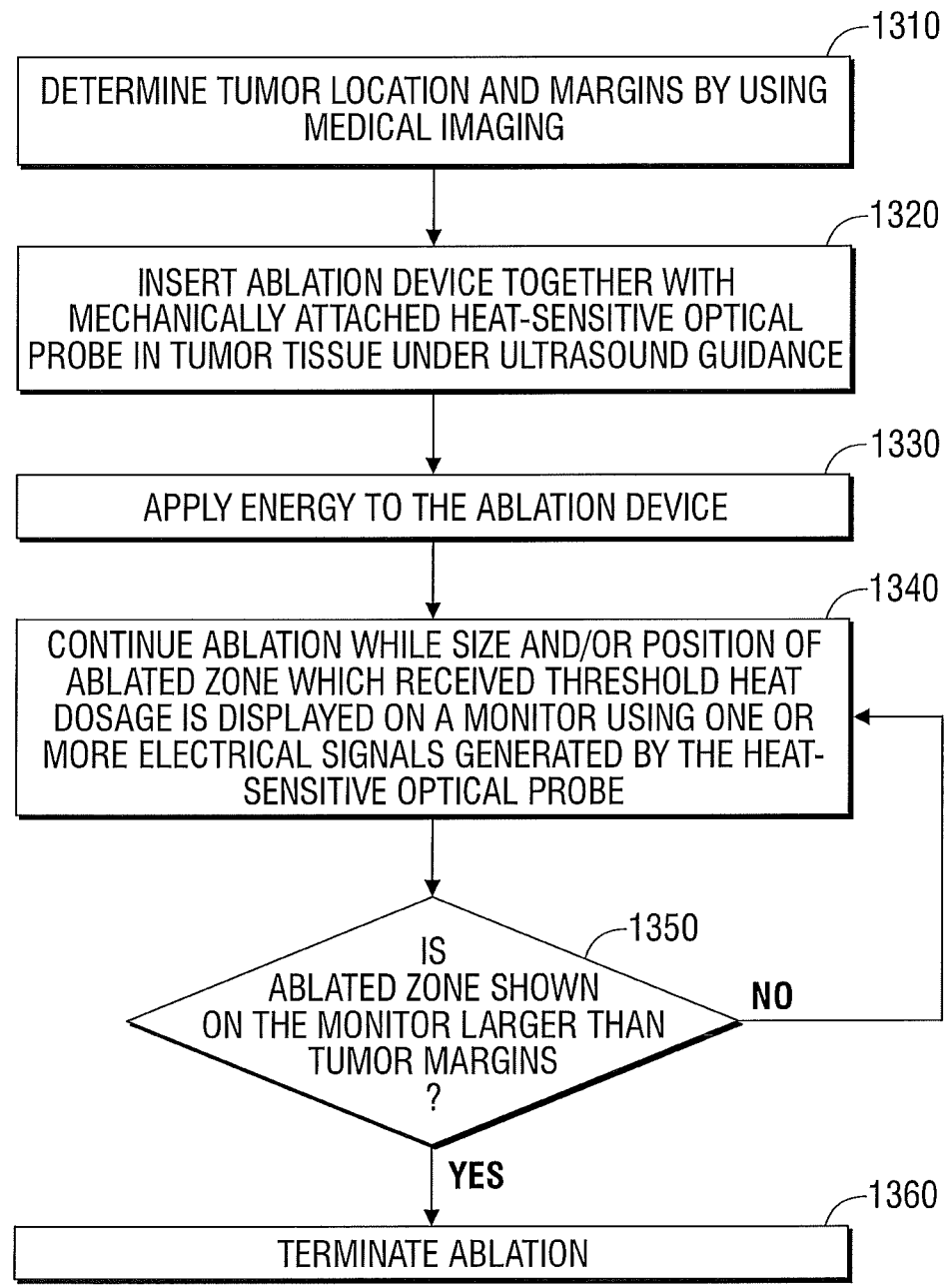
FIG. 13 is a flowchart illustrating a method of directing energy to tissue in accordance with another embodiment of the present disclosure.

FIG. 13 is a flowchart illustrating a method of directing energy to tissue according to an embodiment of the present disclosure. In step 1310, tumor "T" location and/or tumor "T" margins are determined by using medical imaging.

In step 1320, an ablation device (e.g., energy applicator 60) is inserted into tissue "T". Ultrasound guidance may be used to guide the energy applicator 60 into the area of tissue "T" to be treated. The energy applicator 60 is mechanically coupled to a heat-sensitive optical probe 300. Heat-sensitive optical probe 300 is adapted to utilize spectral properties of light to access one or more optical fiber portions (e.g., optical fiber portions "P1", "P2", "P3", "P4", "P5" and "P6") of the heat-sensitive optical probe 300 in response to heat. The energy applicator 60 is operably associated with an electrosurgical power generating source 516.

In step 1340, energy from the electrosurgical power generating source 516 is applied to the energy applicator 60. The electrosurgical power generating source 516 may be capable of generating energy at RF or microwave frequencies or at other frequencies.

In step 1350, ablation continues while the size and/or position of ablated zone which received heat above a certain threshold value is displayed on a monitor using one or more electrical signals generated by the one or more heat-sensitive optical probes 300.

In step 1360, a determination is made whether the ablated zone shown on the monitor is larger than the tumor margins determined in step 1310.

In some embodiments, safety procedures and/or controls, e.g., controls that reduce power level and/or shut off the power delivery to the energy applicator, may be triggered based on the tissue ablation rate and/or assessment of the ablation margins. In some embodiments, a processor unit 526 configured to generate one or more electrical signals for controlling one or more operating parameters associated with an electrosurgical power generating source 516 may be adapted to reduce power level and/or shut off the power delivery based on the tissue ablation rate and/or the proximity of the margins of ablated tissue to the target tissue margins.

The above-described heat-sensitive optical probes, electrosurgical devices and systems, and methods of directing energy to target tissue may be suitable for various open and endoscopic surgical procedures.

The above-described heat-sensitive optical probes may be inserted into or placed adjacent to tissue in a variety of configurations, e.g., to allow visual assessment of ablation margins, or to allow the surgeon to determine the rate of ablation and/or when the procedure has been completed, and/or to trigger safety procedures and/or controls, e.g., controls that reduce power level and/or shuts off the power delivery to the energy applicator.

In the above-described embodiments, one or more operating parameters of an electrosurgical power generating source may be adjusted and/or controlled based on the heat-distribution information provided by the presently-disclosed heat-sensitive optical probes, e.g., to maintain a proper ablation rate, or to determine when tissue has been completely desiccated and/or the procedure has been completed.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. A method of directing energy to tissue, comprising:
    determining a target tissue location and target tissue margins;
    positioning an ablation device for delivery of energy to a target tissue in the target tissue location;
    positioning a heat-sensitive optical probe proximate the target tissue;
    applying energy to the ablation device to treat the target tissue;
    transmitting light to each of a plurality of portions longitudinally spaced along a longitudinal length of the heat-sensitive optical probe;
    determining a degree of heat to which the plurality of portions are exposed based on a change in an optical property of each of the plurality of portions;
    displaying an ablated zone based on the determination of the degree of heat to which each of the plurality of portions is exposed;
    continuing to apply energy to the ablation device while the ablated zone is displayed;
    determining whether the ablated zone displayed is outside the target tissue margins; and
    terminating ablation if it is determined that the ablated zone displayed is outside the target tissue margins.

2. The method of directing energy to tissue of claim 1, wherein the target tissue location and the target tissue margins are determined by using medical imaging.

3. The method of directing energy to tissue of claim 1, wherein determining the degree of heat to which the plurality of portions are exposed includes detecting a change in an optical property of a heat sensitive material disposed along the longitudinal length of the heat-sensitive optical probe in response to exposure to heat.

4. A method of directing energy to tissue, comprising:
    determining a target tissue location and target tissue margins;
    positioning an energy applicator for delivery of energy to a target tissue in the target tissue location;
    positioning a heat-sensitive optical probe proximate the target tissue;
    transmitting energy from an electrosurgical power generating source through the energy applicator to the target tissue;
    acquiring heat-distribution data of the transmitted energy by:
        transmitting light to each of a plurality of portions longitudinally spaced along a longitudinal length of the heat-sensitive optical probe; and
        determining a degree of heat to which the plurality of portions are exposed based on a change in an optical property of each of the plurality of portions;
    determining a tissue ablation rate based on the acquired heat distribution data; and
    determining at least one operating parameter associated with the electrosurgical power generating source based the determined tissue ablation rate.

5. The method of directing energy to tissue of claim 4, wherein the at least one operating parameter associated with the electrosurgical power generating source is selected from the group consisting of temperature, impedance, power, current, voltage, mode of operation, and duration of application of electromagnetic energy.

6. The method of directing energy to tissue of claim 4, wherein determining the degree of heat to which the plurality of portions are exposed includes detecting a change in an optical property of a heat sensitive material disposed along the longitudinal length of the heat-sensitive optical probe in response to exposure to heat.

* * * * *